(12) United States Patent
Hedrick et al.

(10) Patent No.: US 8,926,998 B2
(45) Date of Patent: Jan. 6, 2015

(54) POLYCARBONATES BEARING PENDANT PRIMARY AMINES FOR MEDICAL APPLICATIONS

(75) Inventors: James L. Hedrick, Pleasanton, CA (US); Shrinivas Venkataraman, Singapore (SG); Yi Yan Yang, Singapore (SG)

(73) Assignees: International Business Machines Corporation, Armonk, NY (US); Agency For Science, Technology And Research, Singapore (SG)

(*) Notice: Subject to any disclaimer, the term of this patent is extended or adjusted under 35 U.S.C. 154(b) by 0 days.

(21) Appl. No.: 13/611,116

(22) Filed: Sep. 12, 2012

(65) Prior Publication Data

US 2014/0072607 A1 Mar. 13, 2014

(51) Int. Cl.
*A01N 25/00* (2006.01)
*A61K 31/00* (2006.01)
*A61L 33/00* (2006.01)
*B05D 3/02* (2006.01)

(52) U.S. Cl.
USPC ......... 424/405; 424/78.3; 427/2.1; 427/372.2

(58) Field of Classification Search
None
See application file for complete search history.

(56) References Cited

U.S. PATENT DOCUMENTS

| | | | |
|---|---|---|---|
| 3,223,678 A | | 12/1965 | Bolgiano |
| 3,695,921 A | * | 10/1972 | Shepherd et al. ............. 427/2.28 |
| 4,058,491 A | * | 11/1977 | Steckler ........................ 521/38 |
| 4,443,593 A | | 4/1984 | Collins |
| 5,141,522 A | * | 8/1992 | Landi ............................ 523/114 |
| 5,900,408 A | * | 5/1999 | Block et al. ...................... 514/55 |
| 6,093,792 A | | 7/2000 | Gross et al. |
| 6,316,581 B1 | | 11/2001 | Gross et al. |
| 6,368,658 B1 | * | 4/2002 | Schwarz et al. ............. 427/2.15 |
| 7,728,069 B2 | | 6/2010 | Keul et al. |
| 2006/0029675 A1 | * | 2/2006 | Ginther ........................ 424/486 |
| 2008/0175980 A1 | * | 7/2008 | Sun .............................. 427/2.25 |
| 2010/0305300 A1 | | 12/2010 | Coulembier et al. |
| 2011/0054064 A1 | | 3/2011 | Fukushima et al. |
| 2011/0150977 A1 | | 6/2011 | Hedrick et al. |
| 2011/0151566 A1 | | 6/2011 | Hedrick et al. |
| 2011/0152167 A1 | | 6/2011 | Hedrick et al. |
| 2012/0172559 A1 | | 7/2012 | Hedrick et al. |

FOREIGN PATENT DOCUMENTS

WO 2011078805 A1 6/2011

OTHER PUBLICATIONS

Ding et al. Biomaterials 2012 33:6593-6603.*
Qiao et al. Biomaterials 2012 33:1146-1153.*
Zhou et al. Macromolecular Rapid Communications 2005 26:1309-1314.*
Quinteros et al. European Journal of Pharmaceutical Science 2008 33:72-79.*
Yang et al. Macromolecular Rapid Communications 2011 32:1826-1833.*
Acta Polymerica Sinica 2011 8:889-894 including partial translation.*
Hu, et al., "Aliphatic Poly(ester-carbonate)s Bearing Amino Groups and Its RGD Peptide Grafting", Journal of Polymer Science: Part A: Polymer Chemistry, vol. 46, 7022-7032 (2008), Article first published online: Sep. 24, 2008.
Nederberg_etal, "Biodegradable nanostructures with selective lysis of microbial membranes", NatureChem&Supp, 2011, 3-5, p. 409-414, published online Apr. 3, 2011.
Sanda, et al., "Synthesis and Anionic Ring-Opening Polymerization Behavior of Amino Acid-Derived Cyclic Carbonates", Macromolecules 2001, 34, 1564-1569, Published on Web Feb. 15, 2001.
Korean IPO, International Search Report and Written Opinion, PCT/US2013/057980, date mailed Nov. 27, 2013.
Talal, et al., "One-Step Synthesis of Polycarbonates Bearing Pendant Carboxyl Groups by Lipase-Catalyzed Ring-Opening Polymerization," Journal of Polymer Science: Part A: Polymer Chemistry, vol. 40, 1267-1274 (2002).
Zhang, et al., "Cationic Polycarbonates Prepared Via Michael Addition of Amines of the Pendant Methacrylamido Groups," Acta Polymerica Sinica, 2011, 8, 889-894. Published Online: Aug. 19, 2011. English Abstract.
Allinger, et al., "Organic Chemistry", copyright 1971, published by Worth Publishers, Inc., New York, NY, p. 577.
Carey, F. A. , "Organic Chemistry," fourth edition, published by McGraw Hill Higher Education, New York, New York, copyright 2000, p. 861.
IUPAC Compendium of Chemical Terminology, 2nd ed. (the "Gold Book") (1997), online corrected version: (2006-), internet address http://goldbook.iupac.org/Q05003.html, retrieved Nov. 26, 2013.

* cited by examiner

*Primary Examiner* — Juliet Switzer
*Assistant Examiner* — Caralynne Helm
(74) *Attorney, Agent, or Firm* — Michael R. Roberts

(57) ABSTRACT

An antimicrobial composition comprises an anionic drug and an amine polymer comprising a first repeat unit of formula (2):

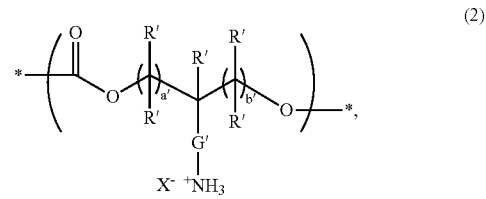

wherein a' is an integer equal to 1 or 2, b' is an integer equal to 1 or 2, and each R' is an independent monovalent radical selected from the group consisting of hydrogen, methyl, ethyl, and combinations thereof. G' is a divalent linking group selected from the group consisting of a single bond and groups comprising at least one carbon. X⁻ is a negatively charged counterion. The drug and the amine polymer are bound by noncovalent interactions.

31 Claims, 5 Drawing Sheets

POLYCARBONATES BEARING PENDANT PRIMARY AMINES FOR MEDICAL APPLICATIONS

PARTIES TO A JOINT RESEARCH AGREEMENT

This invention was made under a joint research agreement between International Business Machines Corporation and the Agency For Science, Technology and Research.

BACKGROUND

The present invention relates to polycarbonates bearing pendant primary amines for medical applications, and more specifically to polycarbonates having a repeat unit derived from serinol, threoninol and like compounds.

A desirable feature of an antimicrobial material for biomedical applications is biodegradability and/or biocompatibility. Peptide based antimicrobials are easily degraded in vivo, and have short blood circulation times, which in part can be attributed to the presence of primary amine groups in their structures. Antimicrobial peptides, however, are disadvantaged by high production costs. Less expensive alternatives are needed.

Polycarbonates bearing protonated amine groups are attractive as biodegradable and/or biocompatible substitutes for peptide-based antibiotics. As one example, cyclic carbonate monomers derived from L-threoninol, in which the primary amine group was protected with a t-butoxy carbonyl (tBoc) group or with a benzyloxy carbonyl (Z) group, were prepared and polymerized by metal catalyzed ring opening polymerization to form homopolymers comprising pendant primary amines (F. Sanda, et al., Macromolecules 2001, 34, pages 1564-1569). However, homopolymers are typically weak antimicrobial agents because of the high charge density.

Other polymers bearing primary amine groups, such as those derived from meth(acrylate) monomers, are limited in their use because of non-biodegradability and/or high cytotoxicity. Many of the existing materials are non-selective biocides (i.e., destructive to microbial and mammalian cells).

Due to the astronomical increase in the development cost of new drug candidates, exploration of innovative tactics for the encapsulation and release of existing drugs has emerged as one of the key approaches to improve the efficacy of treatment. Strategies focusing on the development of novel nano-sized drug delivery platforms have been shown to have tremendous impact in improving the bioavailability of the drugs. Such improvements over the bioavailability of therapeutics will enable effective administration of existing pool of approved drugs.

Comprehensive strategies to manage the drug administration are important, particularly in the following aspects. With respect to antibiotics, the emergence of bacterial resistance and the low rate of regulatory clearance of new antibiotics has created a need to deliver existing antibiotics so as to maximize their efficacy. With respect to non-steroidal anti-inflammatory drugs (NSAID) the increase in the global ageing population has generated a need for optimal use of NSAIDs to alleviate pain. In both of the above-mentioned situations, improper use could lead to long-term detrimental effects. Improper infectious disease management exponentially increases the chances of development of microbial resistance. In the case of NSAIDs, potential development of other side-effects such as gastrointestinal complications may surface.

Thus, biodegradable, biocompatible polymers bearing pendant primary amines were sought as alternatives to peptide based materials for antimicrobial applications and/or the delivery of biologically active substances, such as anionic drugs. Other desirable properties of the polymers include the capability of forming injectable solutions and/or crosslinked hydrogel layers, and high activity against Gram negative microbes in addition to Gram positive microbes.

SUMMARY

Accordingly, an antimicrobial composition is disclosed, comprising:
an anionic drug; and
an amine polymer comprising a first repeat unit of formula (2):

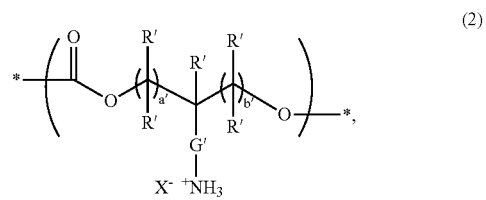

wherein
a' is an integer equal to 1 or 2,
b' is an integer equal to 1 or 2,
each R' is an independent monovalent radical selected from the group consisting of hydrogen, methyl, ethyl, and combinations thereof,
G' is a divalent linking group selected from the group consisting of a single bond and groups comprising at least one carbon,
$X^-$ is a negatively charged counterion, and
the drug and the amine polymer are bound by noncovalent interactions.

Also disclosed is an antimicrobial amine polymer, comprising:
a first repeat unit of formula (4):

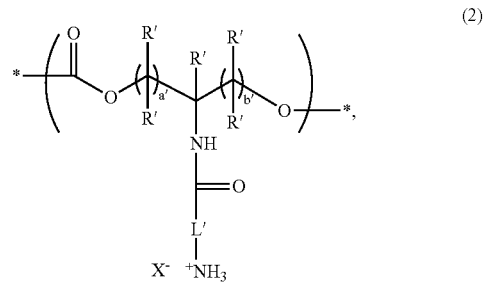

wherein
a' is an integer equal to 1 or 2,
b' is an integer equal to 1 or 2,
each R' is an independent monovalent radical selected from the group consisting of hydrogen, methyl, ethyl, and combinations thereof,
L' is a divalent linking group comprising 2 to 10 carbons, and
$X^-$ is a negatively charged counterion.

Also disclosed is a method, comprising:
providing a mixture comprising i) a first cyclic carbonate monomer, ii) a nucleophilic initiator for ring opening polymerization, iii) an organocatalyst, and iv) a solvent, wherein the first cyclic carbonate monomer has a structure according to formula (6):

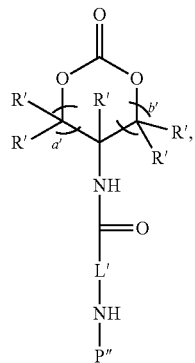

(6)

wherein a' is an integer equal to 1 or 2, b' is an integer equal to 1 or 2, each R' is an independent monovalent radical selected from the group consisting of hydrogen, methyl, ethyl, and combinations thereof, L' is a divalent linking group comprising 2 to 10 carbons, and P'' is a primary amine protecting group;
    agitating the mixture, thereby forming a protected amine polymer by a ring opening polymerization; and
    deprotecting the protected amine polymer, thereby forming an antimicrobial amine polymer.
Further disclosed is a method comprising:
    forming an aqueous mixture containing an amine polymer comprising a first repeat unit of formula (2):

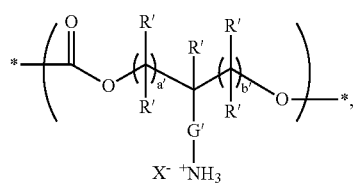

(2)

wherein a' is an integer equal to 1 or 2, b' is an integer equal to 1 or 2, each R' is an independent monovalent radical selected from the group consisting of hydrogen, methyl, ethyl, and combinations thereof, G' is a divalent linking group selected from the group consisting of a single bond and groups comprising at least one carbon, and $X^-$ is a negatively charged counterion;
    forming a second aqueous mixture comprising an anionic drug; and
    combining the first mixture and the second mixture, thereby forming an antimicrobial composition, wherein the amine polymer and the drug are bound by non-covalent interactions.

Also disclosed is a method of treating a microbe, comprising contacting the microbe with the above-described composition, thereby killing the microbe.

Another method is disclosed, comprising disposing the above-described composition on a surface of a substrate and removing any solvent, thereby forming an antimicrobial layer on the surface of the substrate.

Also disclosed is an article comprising the above-described composition disposed on a surface of a medical device.

The above-described and other features and advantages of the present invention will be appreciated and understood by those skilled in the art from the following detailed description, drawings, and appended claims.

DETAILED DESCRIPTION

Figure 1:
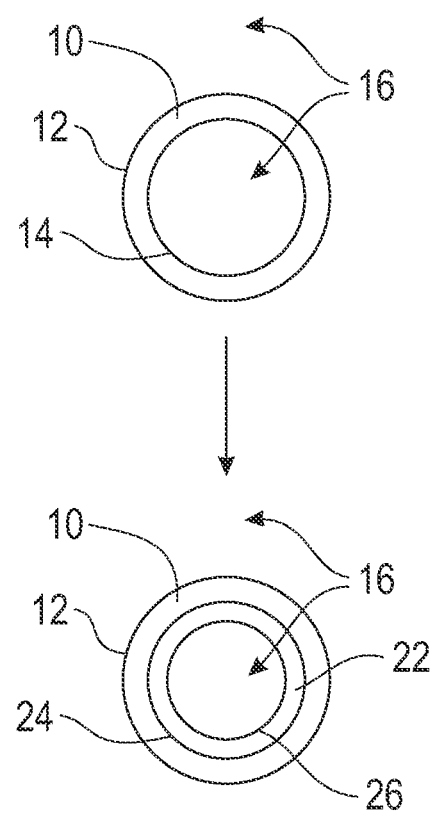
FIG. 1 is a series of schematic layer diagrams demonstrating a method of forming a layer 42 disposed on an inner wall 14 of a tubular substrate 10. Layer 42 comprises an amine polymer comprising pendant protonated amine groups.

The primary amine containing polycarbonates of this invention, referred to for brevity as "amine polymers," have utility as standalone antimicrobial polymers and/or as carriers for the delivery of anionic biologically active materials such as genes, proteins and/or drugs (e.g., anionic antimicrobial drugs). The polycarbonates are prepared by organocatalyzed ring opening polymerization (ROP). The amine polymers are biodegradable, biocompatible, and in some instances are active against Gram negative and Gram positive microbes.

The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the amine polymer of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the amine polymer (i.e., the concentration is below detection limits). In an embodiment, the chemical formulas of the components used to prepare the amine polymer contain none of the above restricted metals.

No restriction is placed on the concentration of boron, silicon, or any individual alkali metal in the amine polymer.

The amine polymers have a repeat unit of formula (1):

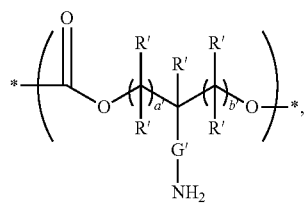

(1)

wherein a' is an integer equal to 1 or 2, b' is an integer equal to 1 or 2, each R' is an independent monovalent radical selected from the group consisting of hydrogen, methyl, ethyl, and combinations thereof, and G' is a divalent linking group selected from the group consisting of a single bond, and groups comprising at least one carbon. In an embodiment, G' is a divalent linking group comprising a nitrogen which is bonded to the polycarbonate backbone.

The pendant primary amine of formula (1) can have the form of a free base (—$NH_2$) or a protonated ammonium salt (—$NH_3^+X^-$), as in the repeat unit of formula (2):

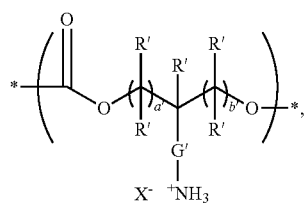

(2)

wherein a', b' R', and G' have the meaning above, and $X^-$ is a negatively charged counterion (e.g., acetate, trifluoroacetate, chloride, bromide). $X^-$ can be a biologically active substance.

The examples further below demonstrate that when G' is a single bond, the amine polymer alone possesses weak or ineffective antimicrobial properties. However, a composition that comprises i) an amine polymer, for which G' is a single bond and ii) an anionic antimicrobial drug, which are bound by noncovalent interactions (e.g., an ionic complex), can be a potent antimicrobial agent that is biodegradable and biocompatible. In these instances, the amine polymer serves as a carrier of the anionic antimicrobial drug. For example, $X^-$ in formula (2) can be exchanged with an anionic antimicrobial drug such as diclofenac or paclitaxel, thereby forming an antimicrobial composition. It will be shown that antimicrobial activity of the amine polymer alone increases by spacing the pendant primary amine group more than one bond from the polymer backbone.

More specific amine polymers comprise a first repeat unit of formula (3):

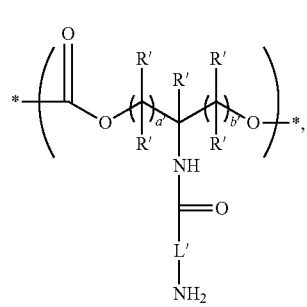

(3)

wherein a' is an integer equal to 1 or 2, b' is an integer equal to 1 or 2, each R' is an independent monovalent radical selected from the group consisting of hydrogen, methyl, ethyl, and combinations thereof, and L' is a divalent linking group comprising 2 to 10 carbons.

The primary amine group of formula (3) can be in the form of hydrosalt as in the repeat unit of formula (4):

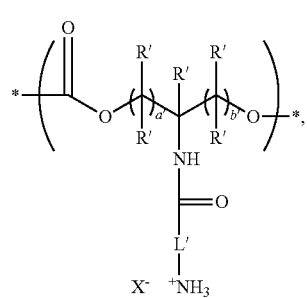

(4)

wherein a', b', R', and L' have the meaning above in formula (3), and $X^-$ is a negatively charged counterion (e.g., chloride, bromide, acetate, and trifluoroacetate). $X^-$ can be a negatively charged biologically active substance.

The negatively charged counterion $X^-$ is preferably an anionic species that is not covalently bound to the chemical structure of the amine polymer. Exemplary negatively charged counterions include, for example, conjugate bases of protic acids. Protic acids have one or more protons, which can be donated to form a hydrosalt of the amine. The hydrosalt comprises a positive charged protonated amine group and a negatively charged conjugate base of the protic acid. Exemplary monoprotic acids include acetic acid, trifluoroacetic acid, and p-toluenesulfonic acid. Exemplary diprotic acids include sulfuric acid and glutamic acid. In an embodiment, the first repeat unit of the amine polymer comprises a hydrosalt of the primary amine group and trifluoroacetic acid.

Amine polymers that contain repeat units of formula (3) and/or formula (4) can be potent antimicrobial materials alone (i.e., $X^-$ not an anionic antimicrobial drug). Moreover, these amine polymers can be active antimicrobial agents when the polymers contain no pendant quaternary amine groups. Additionally, these amine polymers can be toxic to Gram-positive microbes such as *Staphylococcus aureus* (*S. aureus*), Gram negative microbes such as *Escherichia coli* (*E. coli*), fungi, yeasts, and combinations thereof.

In an embodiment, the amine polymer comprises a first repeat unit having a structure:

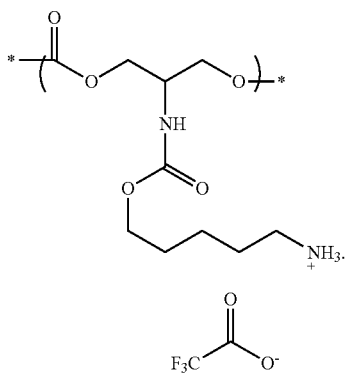

In another embodiment, the amine polymer has a structure:

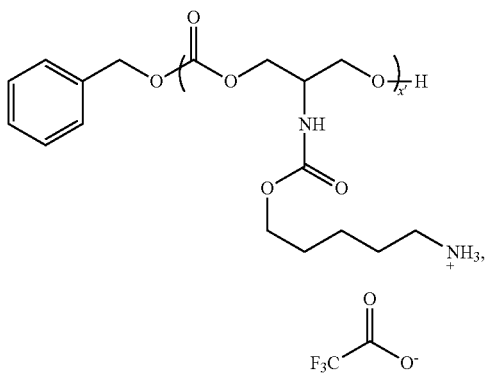

wherein x' is a positive integer having a value of about 15 and 30.

Amine polymers that contain repeat units of formula (3) and/or formula (4) can also serve as carriers for anionic antimicrobial drugs and/or other biologically active materials in the form of a non-covalent nanoparticulate loaded complex. A complex of an amine polymer and an anionic drug can exhibit enhanced antimicrobial properties over the amine polymer alone.

Biologically active substances include cells, biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. Biologically active substances can be used in combination, providing a loaded complex having two or more independent therapeutic functions (e.g., antimicrobial, gene delivery, and/or drug delivery).

Herein "biologically active" means the referenced material can alter the chemical structure and/or activity of a cell in a desirable manner, can selectively alter the chemical structure and/or activity of a cell type relative to another cell type in a desirable manner, and/or provide a medical diagnostic function such as image enhancement. As an example, one desirable change in a chemical structure can be the incorporation of a gene into the DNA of the cell. A desirable change in cellular activity can be the expression of the transfected gene. Another change in cellular activity can be the induced production of a desired hormone or enzyme. Alternatively, a desirable change in cellular activity can be the selective death of one cell type over another cell type. No limitation is placed on the relative change in cellular activity caused by the biologically active substance, providing the change is desirable and useful. Moreover, no limitation is placed on the biologically active substance, providing the biologically active substance induces a useful cellular response when released from the loaded complex. The biologically active substance can comprise a quaternary amine group.

The amine polymer can be a homopolymer, a linear random copolymer, block copolymer comprising 2 or more blocks, a star polymer comprising 6 or more arms, a covalently crosslinked hydrogel comprising a plurality of branches, or a non-crosslinked another branched polymer. An amine polymer that has a triblock structure can form in water an antimicrobial mixed complex by non-covalent interactions with a non-charged second triblock copolymer. As another example, an amine polymer that has a star polymer structure can comprise 6 or more independent block copolymer arms. Each of the arms can comprise a first block comprising a poly(alkylene oxide) backbone linked to a second block comprising the first repeat unit, wherein the first block is linked by an end group to a covalently crosslinked microgel core of the star polymer.

The amine polymer can comprise non-stereospecific and/or stereospecific repeat units. A stereospecific repeat unit i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. For example, if a block B' of a block copolymer A'-B' contains a stereospecific first repeat unit having one asymmetric tetravalent carbon, then the first repeat unit can be present in block B' substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific first repeat unit can be present in block B' substantially as the R,R stereoisomer, substantially as the R,S stereoisomer, substantially as the S,S stereoisomer, or substantially as the S,R stereoisomer.

The amine polymer is preferably prepared by organocatalyzed ring opening polymerization of a first cyclic carbonate monomer bearing a protected primary amine. The reaction mixture for the ring opening polymerization comprises i) the first cyclic carbonate monomer, ii) a nucleophilic initiator for ring opening polymerization, iii) an organocatalyst, and iv) a solvent. The ring opening polymerization produces an intermediate amine polymer comprising a first repeat unit having a pendant protected primary amine. The protected primary amine can be deprotected under mild conditions to form the amine polymer without significant degradation of the polycarbonate backbone.

The first cyclic carbonate monomer has a structure according to formula (5):

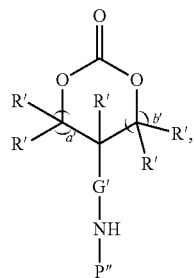
(5)

wherein a' is an integer equal to 1 or 2, b' is an integer equal to 1 or 2, each R' is an independent monovalent radical selected from the group consisting of hydrogen, methyl, ethyl, and combinations thereof, G' is a divalent linking group selected from the group consisting of a single bond, and groups comprising at least one carbon, and P''' is a primary amine protecting group. In an embodiment, G' is a divalent linking group comprising a nitrogen linked to the cyclic carbonate ring.

More specific first cyclic carbonate monomers have a structure according to formula (6):

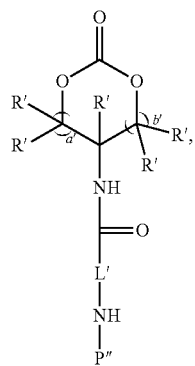
(6)

wherein a' is an integer equal to 1 or 2, b' is an integer equal to 1 or 2, each R' is an independent monovalent radical selected from the group consisting of hydrogen, methyl, ethyl, and combinations thereof, L' is a divalent linking group comprising 2 to 10 carbons, and P''' is a primary amine protecting group. The first cyclic carbonate monomer can be used singularly or in combination with a different first cyclic carbonate monomer.

The first cyclic carbonate monomer can be stereospecific or non-stereospecific. A stereospecific cyclic monomer i) has a non-superposable mirror image and ii) comprises one or more asymmetric tetravalent carbons. A stereospecific cyclic monomer, which includes cyclic carbonate and cyclic ester monomers, has a stereoisomeric purity of 90% or more, and more particularly 98% or more. The asymmetric tetravalent carbons of the stereospecific cyclic monomer can include one or more ring carbons that become polymer backbone carbons in the ring opening polymerization.

Exemplary protecting groups for primary amines include benzyloxycarbonyl (Z), tert-butyloxycarbonyl (tBoc, also written as "Boc" group), and fluorenyloxycarbonyl (Fmoc) as shown in Table 1.

TABLE 1

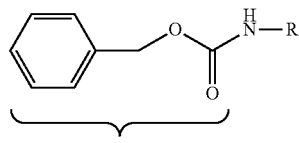
Z

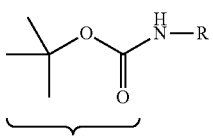
tBoc (Boc)

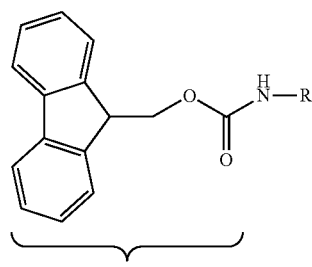
Fmoc

The Z protecting group can be removed by acidolysis or catalytic hydrogenation. The Boc protecting group can be removed by acidolysis. The Fmoc protecting group can be removed by base, typically a secondary amine. In an embodiment, P''' of formula (5) and/or formula (6) is a Boc group. In another embodiment, the Boc-protected primary amine of the intermediate amine polymer is deprotected by treatment of with a fluorinated carboxylic acid. Preferably, the fluorinated carboxylic acid is trifluoroacetic acid.

Specific first cyclic carbonate monomers include tBuODC, which can be represented by the structures:

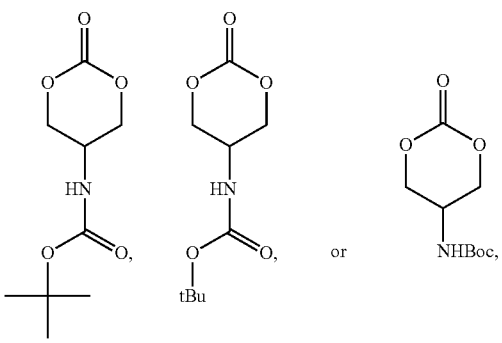

can be prepared by phosgenation of the commercially available N-Boc-serinol:

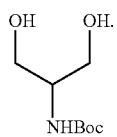

The amine polymer derived from tBuODC has a first repeat unit (after deprotection) having the structure:

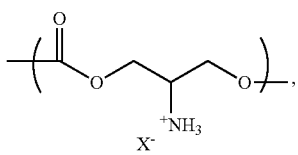

wherein X⁻ is a negatively charged counterion. X⁻ can be an anionic drug.

Similarly, tBuMODC, which has the structure

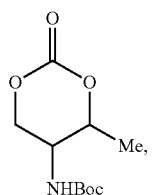 [SMILES: CC1OC(=O)OCC1NC(=O)OC(C)(C)C]

can be prepared by phosgenation of commercially available N-Boc-threoninol:

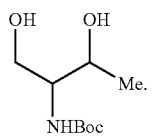

The amine polymer derived from tBuMODC has a first repeat unit (after deprotection) having the structure:

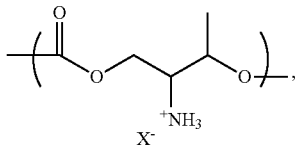

wherein X⁻ is a negatively charged counterion that can include an anionic drug. Stereochemistry is not shown.

N-Boc-L-threoninol, shown below with (R,R) stereochemistry can be used to prepare a stereospecific cyclic carbonate monomer L-tBuMODC comprising a protected primary amine group:

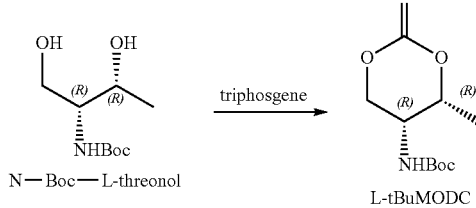

The first repeat unit comprising the protonated primary amine group is present in the amine polymer in an amount of about 20 mol % to 100 mol % based on total moles of cyclic carbonyl monomers used to prepare the amine polymer.

In addition to the first cyclic carbonate monomer, the reaction mixture for the ring opening polymerization can also comprise one or more cyclic carbonyl comonomers selected from the group consisting of cyclic carbonates, cyclic esters (lactones), and combinations thereof. A cyclic carbonyl comonomer can serve, for example, as a diluent to adjust hydrophobicity and/or hydrophilicity of the ring opened polymer chain. The cyclic carbonyl comonomer can be stereospecific or non-stereospecific. The cyclic carbonyl comonomer can comprise a protected amine, which can be deprotected after the polymerization.

Exemplary cyclic carbonyl comonomers include the compounds of Table 2.

TABLE 2

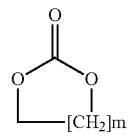

m = 1: Trimethylene carbonate (TMC)
m = 2: Tetramethylene carbonate (TEMC)
m = 3: Pentamethylene carbonate (PMC)

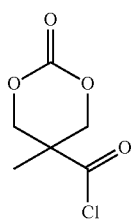

MTCCl

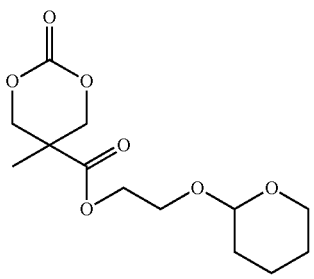 [SMILES: CC1(C(=O)OCCOC2CCCCO2)COC(=O)OC1]

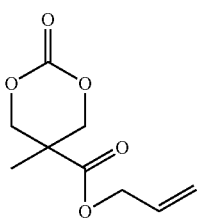

(MTCTFE)

TABLE 2-continued
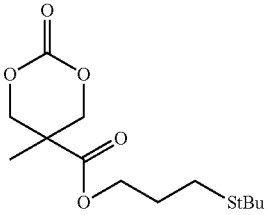
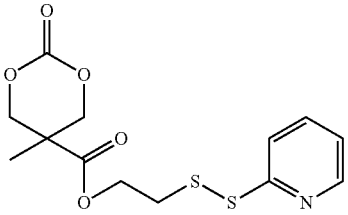 [SMILES: CC1(C(=O)OCCSSc2ccccn2)COC(=O)OC1]
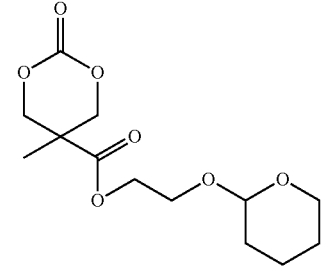 [SMILES: CC1(C(=O)OCCOC2CCCCO2)COC(=O)OC1]
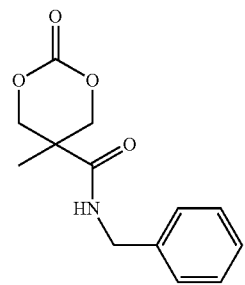 [SMILES: CC1(C(=O)NCc2ccccc2)COC(=O)OC1]
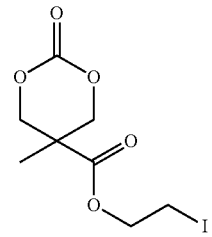
MTCOEtI
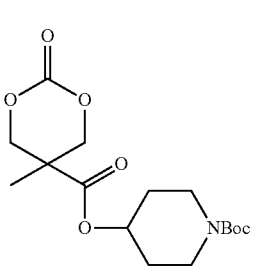 [SMILES: CC(C)(C)OC(=O)N1CCC(OC(=O)C2(C)COC(=O)OC2)CC1]
TABLE 2-continued
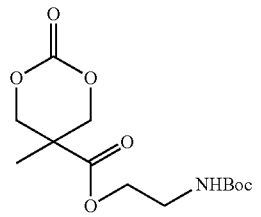 [SMILES: CC(C)(C)OC(=O)NCCOC(=O)C1(C)COC(=O)OC1]
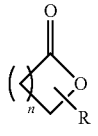
R = H, n = 1: beta-Propiolactone (b-PL)
R = H, n = 2: gamma-Butyrolactone (g-BL)
R = H, n = 3: delta-Valerolactone (d-VL)
R = H, n = 4: epsilon-Caprolactone (e-CL)
R = CH$_3$, n = 1: beta-Butyrolactone (b-BL)
R = CH$_3$, n = 2: gamma-Valerolactone (g-VL)
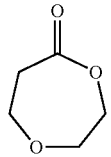
1,5-Dioxepan-2-one
(DXO)
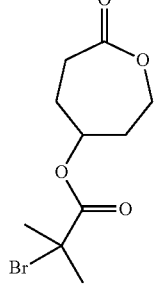
7-Oxooxepan-4-yl 2-bromo-2-methylpropanoate
(BMP-XO)
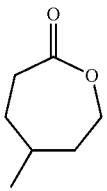
5-Methyloxepan-2-one
(MXO)

TABLE 2-continued
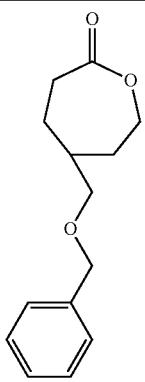
5-(Benzyloxymethyl)oxepan-2-one (BOMXO)
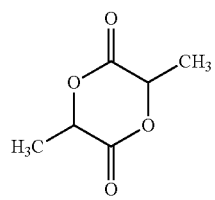
D-Lactide (DLA),
L-Lactide (LLA), or
racemic Lactide, 1:1 D:L forms (DLLA)
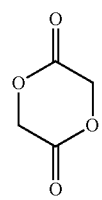
Glycolide (GLY)
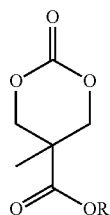
R = hydrogen (MTCOH)
R = methyl (MTCOMe)
R = t-butyl (MTCO'Bu)
R = ethyl (MTCOEt)
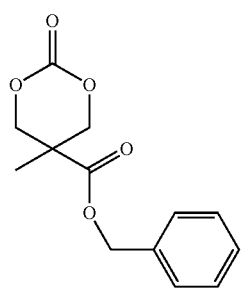 [SMILES: CC1(C(=O)OCc2ccccc2)COC(=O)OC1]
MTCOBn
TABLE 2-continued
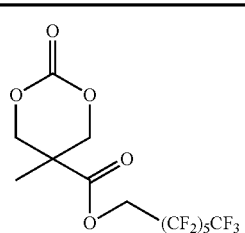
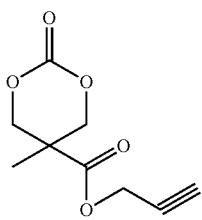
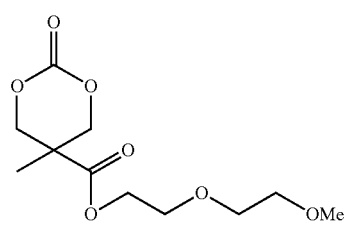 [SMILES: COCCOCCOC(=O)C1(C)COC(=O)OC1]
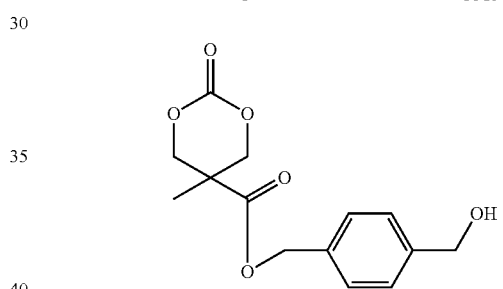
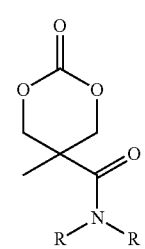
R = methyl
R = iso-propyl
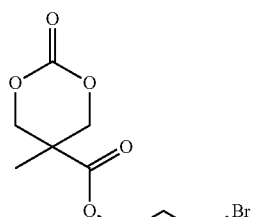
MTCOPrBr TABLE 2-continued

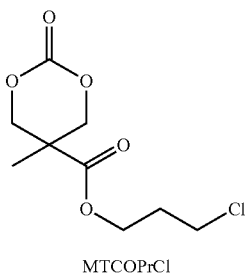

MTCOPrCl

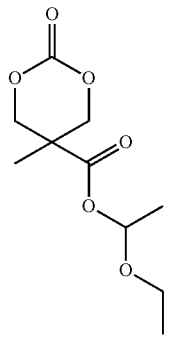 [SMILES: CCOC(C)OC(=O)C1(C)COC(=O)OC1]

MTCOEE

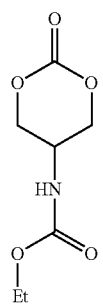

EtODC

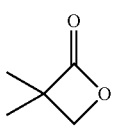

Pivalolactone
(PVL)

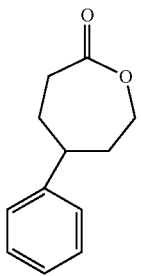 [SMILES: O=C1CCC(c2ccccc2)CCO1]

5-(Benzyloxy)oxepan-2-one
(BXO)

TABLE 2-continued

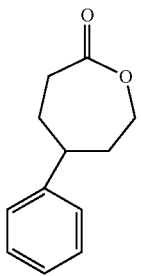 [SMILES: O=C1CCC(c2ccccc2)CCO1]

5-Phenyloxepan-2-one
(PXO)

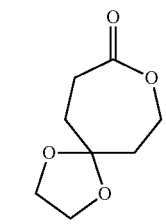 [SMILES: O=C1CCC2(CCO1)OCCO2]

1,4,8-Trioxa(4,6)spiro-9-undecane
(TOSUO)

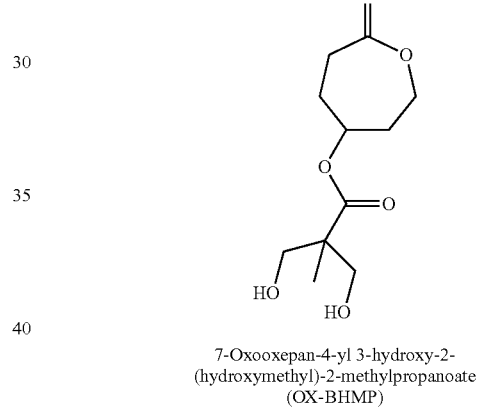

7-Oxooxepan-4-yl 3-hydroxy-2-
(hydroxymethyl)-2-methylpropanoate
(OX-BHMP)

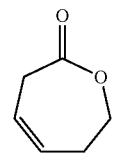

(Z)-6,7-Dihydrooxepin-2(3H)-one
(DHXO)

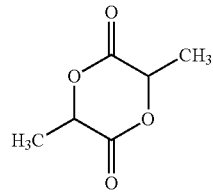

meso-Lactide (MLA)
(two opposite centers of asymmetry,
R and S)

The above cyclic carbonyl comonomers can be purified by recrystallization from a solvent such as ethyl acetate or by other known methods of purification, with particular attention being paid to removing as much water as possible from the comonomer. The comonomer moisture content can be from 1 to 10,000 ppm, 1 to 1,000 ppm, 1 to 500 ppm, and most specifically 1 to 100 ppm, by weight of the monomer.

ROP Initiators

The ROP reaction mixture comprises an initiator. The initiator becomes a chain fragment that is covalently linked to a repeat unit of the ring opened polymer chain. Initiators for ring opening polymerizations generally include nucleophilic groups such as alcohols, primary amines, secondary amines, thiols, and combinations thereof. The initiator can comprise one or more active nucleophilic initiator groups. The initiator can be polymeric or non-polymeric. For example, the initiator can be a polymeric alcohol, polymeric amine, or polymeric thiol.

More particularly, the initiator for the ring opening reaction is an alcohol. The alcohol initiator can be any suitable alcohol, including mono-alcohol, diol, triol, or other polyol. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, or a combination thereof. Monomeric diol initiators include ethylene glycols, propylene glycols, hydroquinones, and resorcinols. Another example of a diol initiator is BnMPA, derived from 2,2-dimethylol propionic acid.

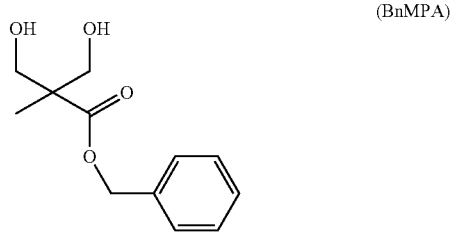 [SMILES: CC(CO)(CO)C(=O)OCc1ccccc1]

(BnMPA)

BnMPA is a precursor used in the preparation of cyclic carbonate monomers.

The initiator can include protected nucleophilic ROP initiator groups that include protected thiols, protected amines, and protected alcohols.

Exemplary polymeric mono-nucleophilic ROP initiators include mono-endcapped poly(ethylene glycols) (e.g., mono-methyl poly(ethylene glycol) (mPEG-OH)) and mono-endcapped poly(propylene glycols).

Exemplary dinucleophilic polyether ROP initiators include poly(ethylene glycol) (referred to as PEG or HO-PEG-OH) having the structure HO—[CH$_2$CH$_2$O]$_n$—H and poly(propylene glycol) (referred to as PPG or HO-PEG-OH) having the structure HO—[CH$_2$C(H)(CH$_3$)O]$_n$—H (HO-PPG-OH), and copolyethers comprising ethylene oxide and propylene oxide repeat units.

The number average molecular weight (Mn) of the dinucleophilic polyether initiator can be from 100 to 10000 Da, and even more specifically, 1000 to 5000 Da.

In an embodiment, the initiator is a mono-endcapped poly(alkylene glycol), such as mono-methyl endcapped polyethylene glycol (mPEG-OH), which is commercially available in different average molecular weights.

Endcap Agents

Endcapping the intermediate amine polymer (i.e., prior to deprotection) or the amine polymer is optional. An endcap agent can prevent further chain growth and stabilize the reactive end groups, minimizing unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can also be a biologically active moiety.

Ring Opening Polymerizations (ROP)

The following description of methods, conditions and materials for ring opening polymerizations is applicable to the preparation of the amine polymer and other ROP components of the antimicrobial composition.

The ring-opening polymerization can be performed at a temperature that is about ambient temperature or higher, 15° C. to 40° C., and more specifically 20° C. to 40° C. Reaction times vary with solvent, temperature, agitation rate, pressure, and equipment, but in general the polymerizations are complete within 1 to 100 hours.

The ROP reaction is performed with a solvent. Solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted under an inert (i.e., dry) atmosphere, such as nitrogen or argon, and at a pressure of from 100 to 500 MPa (1 to 5 atm), more typically at a pressure of 100 to 200 MPa (1 to 2 atm). At the completion of the reaction, the solvent can be removed using reduced pressure.

The catalyst is an organocatalyst whose chemical formula contains none of the restricted metals described further above. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexyl-thiourea (TU):

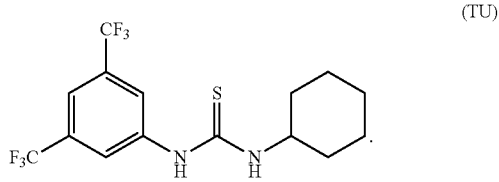 [SMILES: FC(F)(F)c1cc(NC(=S)NC2CCCCC2)cc(C(F)(F)F)c1]

(TU)

Other ROP organocatalysts comprise at least one 1,1,1,3,3,3-hexafluoropropan-2-ol-2-yl (HFP) group. Singly-donating hydrogen bond catalysts have the formula (7):

$$R^2\text{—C}(CF_3)_2OH \qquad (7),$$

wherein R² represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 3.

TABLE 3

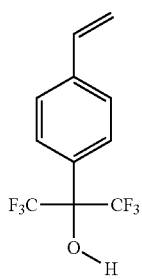

4-HFA-St

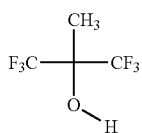

HFTB

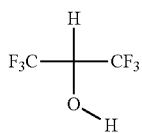

HFIP

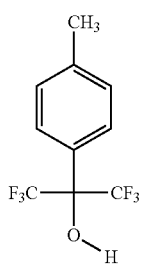

4-HFA-Tol

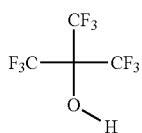

NFTB

Doubly-donating hydrogen bonding catalysts have two HFP groups, represented by the general formula (8):

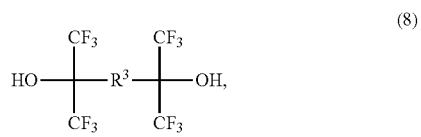

(8)

wherein R³ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (8) include those listed in Table 4. In a specific embodiment, R² is an arylene or substituted arylene group, and the HFP groups occupy positions meta to each other on the aromatic ring.

TABLE 4

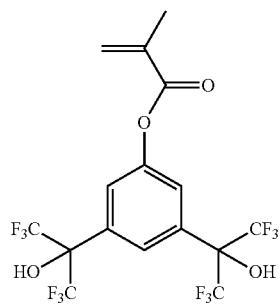 [SMILES: C=C(C)C(=O)Oc1cc(C(O)(C(F)(F)F)C(F)(F)F)cc(C(O)(C(F)(F)F)C(F)(F)F)c1]

3,5-HFA-MA

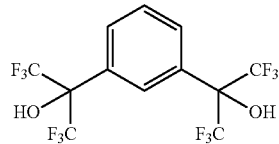

1,3-HFAB

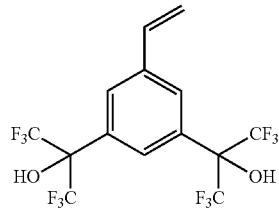 [SMILES: C=Cc1cc(C(O)(C(F)(F)F)C(F)(F)F)cc(C(O)(C(F)(F)F)C(F)(F)F)c1]

3,5-HFA-St

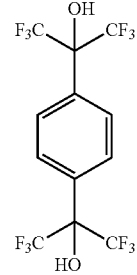

1,4-HFAB

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha,alpha,alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, two or more organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane ($Me_2NCy$), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 5.

TABLE 5

Pyridine
(Py)

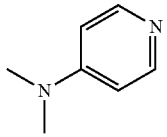

4-N,N-Dimethylaminopyridine
(DMAP)

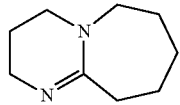

TABLE 5-continued 1,8-Diazabicyclo[5.4.0]undec-7-ene
(DBU)

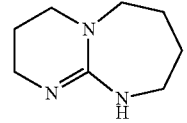

1,5,7-Triazabicyclo[4.4.0]dec-5-ene
(TBD)

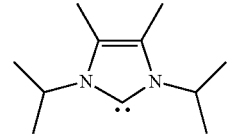

1,3-Bis(2-propyl)-4,5-dimethylimidazol-
2-ylidene
(Im-1)

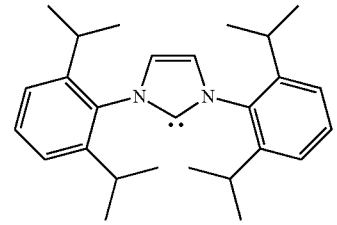 [SMILES: CC(C)c1cccc(C(C)C)c1N1C=CN(c2c(C(C)C)cccc2C(C)C)C1]

1,3-Bis(2,6-di-i-propylphenyl(imidazol-2-ylidene
(Im-3)

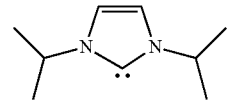

1,3-Di-i-propylimidazol-2-ylidene
(Im-5)

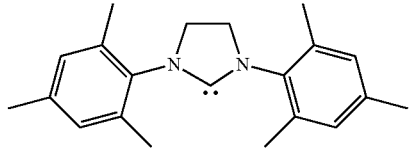

1,3-Bis(2,4,6-trimethylphenyl)-4,5-
dihydroimidazol-2-ylidene
(Im-7)

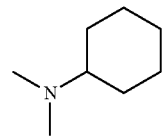

N,N-Dimethylaminocyclohexane
($Me_2NCy$)

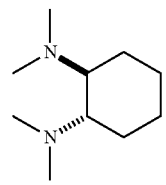

TABLE 5-continued

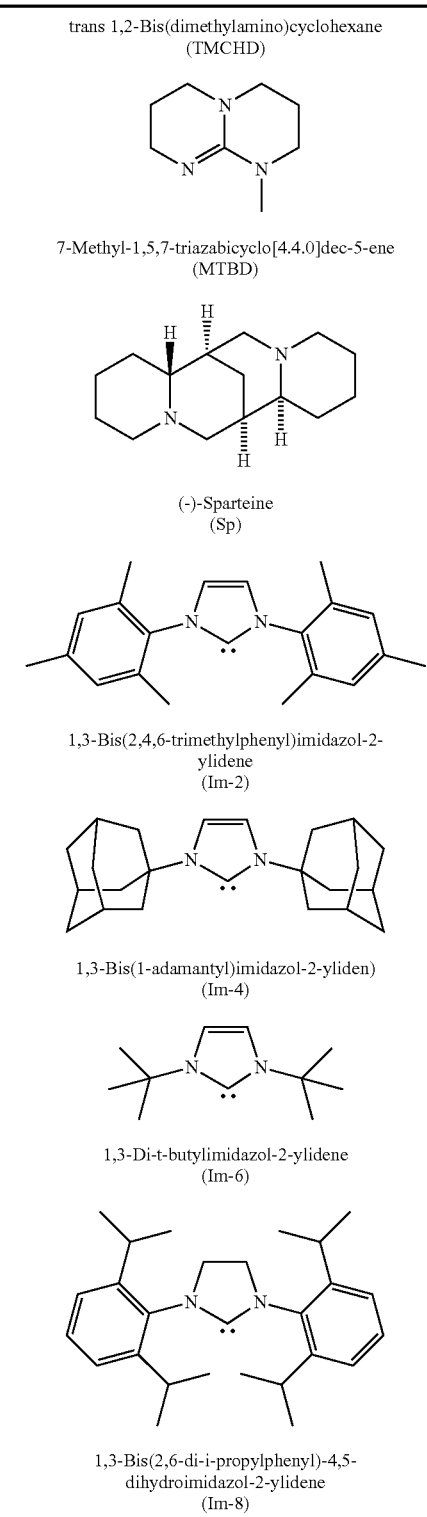

trans 1,2-Bis(dimethylamino)cyclohexane
(TMCHD)

7-Methyl-1,5,7-triazabicyclo[4.4.0]dec-5-ene
(MTBD)

(−)-Sparteine
(Sp)

1,3-Bis(2,4,6-trimethylphenyl)imidazol-2-ylidene
(Im-2)

1,3-Bis(1-adamantyl)imidazol-2-yliden)
(Im-4)

1,3-Di-t-butylimidazol-2-ylidene
(Im-6)

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per participating nucleophilic initiator group in the ring opening polymerization. The participating initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomers used in the polymerization. For example, if the molecular weight of the initiator is 100 g/mole and the initiator has two participating hydroxyl initiator groups, the equivalent molecular weight per hydroxyl group is 50 g/mole. If the polymerization calls for 5 mol % reactive hydroxyl groups per mole of cyclic carbonyl monomers, the amount of initiator is 0.05×50=2.5 g per mole of cyclic carbonyl monomers.

In a specific embodiment, the catalyst is present in an amount of about 0.2 to 20 mol %, the nitrogen base accelerator is present in an amount of 0.1 to 5.0 mol %, and the participating nucleophilic initiator groups of the initiator are present in an amount of 0.1 to 5.0 mol % based on the equivalent molecular weight per participating nucleophilic initiator group of the initiator.

The catalysts can be removed by selective precipitation or in the case of the solid supported catalysts, simply by filtration. The intermediate amine polymer can comprise residual catalyst in an amount greater than 0 wt. % (weight percent), based on total weight of the precursor amine polymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the precursor amine polymer and the residual catalyst.

Average Molecular Weight

The amine polymer and/or the intermediate amine polymer preferably have a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the amine polymer and/or the intermediate amine polymer has a number average molecular weight of 4,000 to 15,000 g/mole. The amine polymer and/or the precursor amine polymer also preferably has a narrow polydispersity index (PDI), generally from 1.01 to 2.0, more particularly 1.01 to 1.30, and even more particularly 1.01 to 1.25.

Industrial Applicability

The amine polymers can be used alone or in the form of a complex (loaded complex) with a variety of biologically active substances including genes, proteins, and/or drugs. A method comprises contacting a microbe with the amine polymer and/or loaded complex, thereby killing the microbe. The amine polymer and the biologically active substance are bound by non-covalent interactions. The biologically active substance can be encapsulated into the core of a micellar nanostructure formed by the amine polymer in water. For example, amine polymers comprising a poly(ethylene oxide) chain can form loaded complexes via electrostatic interactions between the anionic residues present in the drugs and the cationic polymers. The encapsulation process can be conducted in an aqueous mixture without employing potentially toxic organic solvents. The combination of polymer biocompatibility, structural versatility, and nano-sized drug loaded particles provides for effective delivery of anionic therapeutics. In an embodiment, a loaded complex comprises the amine polymer and the drug diclofenac (DCF) or the drug penicillin G (PenG).

The antimicrobial compositions comprising the amine polymer and/or a loaded complex of the amine polymer can have a variety of forms, such as powders, fluid solutions (e.g., aqueous micelle solutions), viscous fluids, hydrogels, pastes, creams, and/or films.

The amine polymer and optionally a biologically active material can include many types of chemical functionality in a biodegradable structure, providing a wide range of applications for these materials. For example, the composition can be an injectable solution, or a mixture which is disposed as an antimicrobial film layer on a variety of medically useful substrates. The layer can be effective in inhibiting the growth of at least a Gram-positive microbe.

Substrates can comprise materials such as cloth, gauze, glass, metal, plastic, and combinations thereof. Substrates can have any shape or contour suitable for disposing the compositions.

The substrate can be a medical device. Medical devices include bandages, gauzes, catheters, swabs, catheters, sutures, stents, bedpans, gloves, facial masks, absorbent pads, absorbent garments, internal absorbent devices, artificial organs, medical instruments and insertable mechanical devices. In an embodiment, an article comprises a layer comprising an amine polymer and a biologically active substrate disposed on a surface of a medical device. In another embodiment the medical device is a catheter. In another embodiment, the medical device is a material suitable for a wound dressing, such as gauze.

In an exemplary method illustrated in the schematic layer diagrams of FIG. 1, a mixture comprising an amine polymer is disposed on an inner wall 14 (concave surface) of a tubular substrate 10 (e.g., a catheter), thereby forming layer 22 comprising the amine polymer and the biologically active material. Air 16 is indicated and interface 24. Tubular substrate 10 also has outer wall 12 (convex surface) exposed to air 16.

The compositions can be deposited on a substrate in the form of a liquid coating mixture (e.g., aqueous solution) using any suitable technique, for example dip coating, brush coating, injection coating, spin coating, spray coating, and combinations thereof.

Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRONT™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

In an embodiment, the loaded complex comprises a drug selected from the group consisting of β-lactam antibiotics and non-steroidal anti-inflammatory drugs (NSAIDs) for infectious diseases and pain management, respectively.

The examples further below demonstrate the antimicrobial properties of the amine polymers against Gram-negative microbes, such as *Esherichia Coli* (*E. coli*), and Gram-positive microbes, such as *Staphylococcus aureus* (*S. aureus*), fungi, and yeast. Loaded complexes were prepared with penicillin G (PenG) or diclofenac (DFC).

In some instances, the amine polymers alone are effective antimicrobial agents. In a specific embodiment, an antimicrobial amine polymer is a homopolymer of the first repeat unit of formula (4), the homopolymer having a monomeric alkoxy end group or a monomeric aryloxy end group (a residue of a non-polymeric ROP initiator having one alcohol group). The amine polymer can have a degree of polymerization of about 15 to 45, more specifically about 20 to about 40. This amine polymer can be an effective antimicrobial agent against at least *E. coli* and *S. aureus*.

In another specific embodiment, the amine polymer is a linear random copolymer consisting essentially of the first repeat unit of formula (4) and a hydrophobic second repeat unit comprising an ester or carbonate backbone group, wherein the linear random copolymer has a monomeric alkoxy end group or monomeric aryloxy end group. The linear random copolymer can have a degree of polymerization of about 10 to about 30, more specifically about 20 to about 30. The linear random copolymer can comprise the first repeat unit in an amount of about 45 mol % to about 75 mol % based on total moles of repeat units of the linear random copolymer chain. The linear random copolymer can comprise the hydrophobic second repeat unit in an amount of about 55 mol % to about 25 mol % based on total moles of repeat units of the linear random copolymer chain. This amine polymer can be an effective antimicrobial agent against at least *E. coli* and *S. aureus*.

Herein, $M_n$ is the number average molecular weight, $M_w$ is the weight average molecular weight, and MW is the molecular weight of one molecule.

Unless specifically mentioned, all materials were purchased from Sigma-Aldrich or TCI. All solvents were of analytical grade, purchased from Fisher Scientific or J. T. Baker and used as received. Benzyl alcohol, 1,8-diazabicyclo[5.4.0]undec-7-ene (DBU), and (−)-sparteine were distilled from $CaH_2$ under dry $N_2$ and transferred to glove box. Before transferring into glove box, monomers and other reagents (e.g., mPEG-OH) were dried extensively by freeze drying process under high vacuum.

N-bis(3,5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Nuclear Magnetic Resonance (NMR) Spectroscopy

The $^1$H- and $^{13}$C-NMR spectra of monomers and polymers were recorded using a Broker Avance 400 spectrometer, and operated at 400 and 100 MHz respectively, with the solvent proton signal as the internal reference standard.

Molecular Weight Determination by Size Exclusion Chromatography (SEC)

SEC was conducted using THF as the eluent for monitoring the polymer conversion and also for the determination of polystyrene equivalent molecular weights of the macro-transfer agents. THF-SEC was recorded on a Waters 2695D Separation Module equipped with a Waters 2414 differential refractometer and Waters HR-4E and HR-1 columns. The system was equilibrated at 30° C. in THF, which served as the polymer solvent and eluent with a flow rate of 1.0 mL/minute. Polymer solutions were prepared at a known concentration (about 3 mg/mL) and an injection volume of 100 microliters was used. Data collection and analysis were performed using the Astra software (Wyatt Technology Corporation, USA; version 5.3.4.14). The columns were calibrated with series of polystyrene standards ranging from $M_p$=360 Da to $M_p$=778 kDa (Polymer Standard Service, USA).

Transmission Electron Microscopy (TEM)

The morphologies of drug-loaded nanostructures were observed under a FEI Tecnai G2 F20 electron microscope using an acceleration voltage of 200 keV. The TEM samples were prepared by first placing a drop of aqueous polymer

EXAMPLES

Materials used in the following examples are listed in Table 6.

TABLE 6

| ABBREVIATION | DESCRIPTION | SUPPLIER |
|---|---|---|
| mPEG-OH | Mono-Methyl Poly(ethylene glycol) (Mn 5000 Da) | PolymerSource Inc. |
| Serinol | 2-Amino-1,3-Propanediol, MW 91.11 | Sigma-Aldrich or TCI |
| N-Boc-Serinol | 1,1-Dimethylethyl [2-hydroxy-1-(hydroxymethyl)ethyl]carbamate, MW 191.22 | Sigma-Aldrich |
| TU | N-bis(3,5-bis(trifluoromethyl)-phenyl)-3-cyclohexyl-2-thiourea | Prepared below |
| DBU | 1,8-Diazabicyclo[5,4,0]undec-7-ene | Sigma-Aldrich |
| Bis-MPA | 2,2-Bis(hydroxymethyl)propionic Acid | Sigma-Aldrich |
| 4Arm-PEG-OH | $C[CH_2O(CH_2CH_2O)_{m-1}CH_2CH_2OH]_4$ Mw 10,000, sold under the tradename 4-Arm PEG-OH, m is approximately 55 | Creative PEGWorks, USA |
| Sparteine | (6R,8S,10R,12S)-7,15-Diazatetracyclo[7.7.1.0$^{2,7}$.0$^{10,15}$]heptadecane; (−)-Sparteine | Sigma-Aldrich |
| TFA | Trifluoroacetic Acid | Sigma-Aldrich |
| BzOH | Benzyl Alcohol | Sigma-Aldrich | solution (4.0 microliters) onto a formvar coated 200 mesh copper grid (Ted Pella Inc., USA). After 1 minute, the excess solution was wicked off by using filter paper. Then the staining agent phosphotungstic acid (2% w/v; 4.0 microliters) was placed on the grid and after a minute, the excess solution was wicked off and the grid was left to dry under the ambient conditions.

Monomer Synthesis

EXAMPLE 1

Synthesis of tert-butyl 2-oxo-1,3-dioxan-5-ylcarbamate (tBuODC)

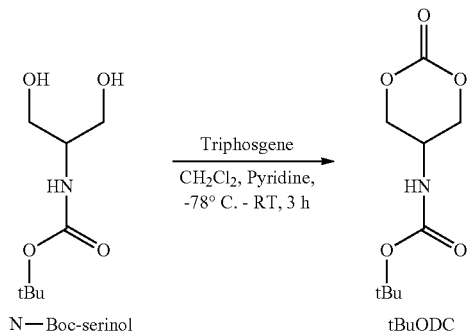

A cyclic carbonate monomer derived from L-threonine that bears a pendant tBoc-protected primary amine is known, but this monomer is less preferred than the corresponding benzyl-protected cyclic carbonate monomer due to the hydrophobic methyl group of threonine. This limitation of the threonine based cyclic carbonate monomers was found not to exist with respect to corresponding serine-based cyclic carbonate monomer, as follows.

N-Boc-serinol (2.00 g, 10.5 mmol, 1.0 equivalent) was suspended in anhydrous dichloromethane (15 mL) in a round bottom flask (50 mL) and pyridine (5.1 mL, 63.3 mmol, 6.0 equivalents) was added to the suspension. Immediately after the addition of pyridine, N-boc-serinol dissolved to form a homogeneous solution, which was cooled in a dry ice-acetone bath (−78° C.). To this cooled reaction mixture, triphosgene (1.78 g, 6.0 mmol, 1.7 equivalents, based on functional equivalents of triphosgene) solution (dissolved in 10 mL of dichloromethane) was added dropwise over 15 minutes. After 1 hour at −78° C., the reaction mixture was allowed to warm to room temperature, and after 2 hours, the reaction was quenched by adding aqueous ammonium chloride solution (10 mL). The organic layer was washed twice with deionized (DI) water (50 mL) and once with 10% NaCl solution (50 mL), and dried using $Na_2SO_4$. Removal of solvent by vacuum resulted in crude product as a yellow solid (1.82 g, 80%). The crude product was further purified by recrystallization from tetrahydrofuran:diethyl ether (10:90 to 20:80 v/v) (60 mL), resulting in a white crystalline solid (1.29 g, 57%).

A model deprotection reaction was conducted on the cyclic monomer tBuODC in the presence of TFA that confirmed the mild acid used to cleave the tBoc groups did not ring-open the cyclic carbonate functionality (reaction shown below).

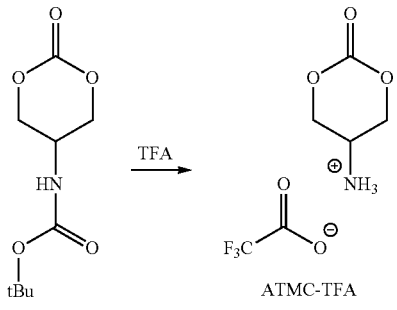

In a 20 mL scintillation vial with magnetic stir bar, tBuODC (1.32 g) was mixed with trifluoroacetic acid (TFA) (3.0 mL) and dichloromethane (DCM) (3.0 mL). The reaction was allowed to stir for about 1 hr at ambient temperature and the reaction mixture turned from clear to cloudy. Upon removal of DCM and excess TFA in vacuo, $^1$H NMR spectroscopy was used to confirm the complete removal of tBoc groups, producing 5-ammonio-trimethylenecarbonate trifluoroacetate (ATMC-TFA).

The deprotected-cyclic carbonate monomer ATMC-TFA can serve as an excellent starting point for the preparation of numerous classes of functional carbonate monomers through the reactions of the amine with functional iso(thio)cyanates, acids, acid anhydrides, acid halides, haloformates, aldehydes and ketones.

EXAMPLE 2

Synthesis of ethyl 1,3-dihydroxypropan-2-yl-carbamate, (EtDHPC)

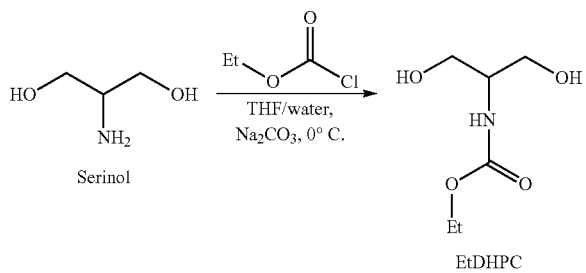 [SMILES: NC(CO)CO ; CCOC(=O)Cl ; CCOC(=O)NC(CO)CO]

In a 1 liter round bottom flask with magnetic stir bar, serinol (10.0 g) and $Na_2CO_3$ (25.0 g) were dissolved in the mixture of DI water (250 mL) and THF (150 mL). The reaction mixture was allowed to cool in ice. Ethyl chloroformate (10.5 mL) was added drop-wise and the reaction was allowed to proceed in ice for 4 hours, followed by about 16 hours at room temperature. Another 100 mL of DI water was added to the reaction mixture and the product was extracted into ethyl acetate (20×100 mL). The crude product (11.6 g) was further purified by flash column chromatography, using silica as the packing material and $CH_3OH:CHCl_3$ (1:9) mixture as the eluent. The final product was a transparent viscous oil that was crystallized in the presence of trace ethyl acetate (1 to 2 mL) along with vigorous scratching using a spatula. The crystallized product was washed with cold ethyl acetate:hexanes (1:1) mixture (1×100 mL), and dried under vacuum to result in white crystalline solid (8.9 g, 54.5%).

EXAMPLE 3

Isobutyl 1,3-dihydroxypropan-2-yl-carbamate (iBuDHPC) was prepared using serinol and isobutyl chloroformate according to the general procedure described in Example 2.

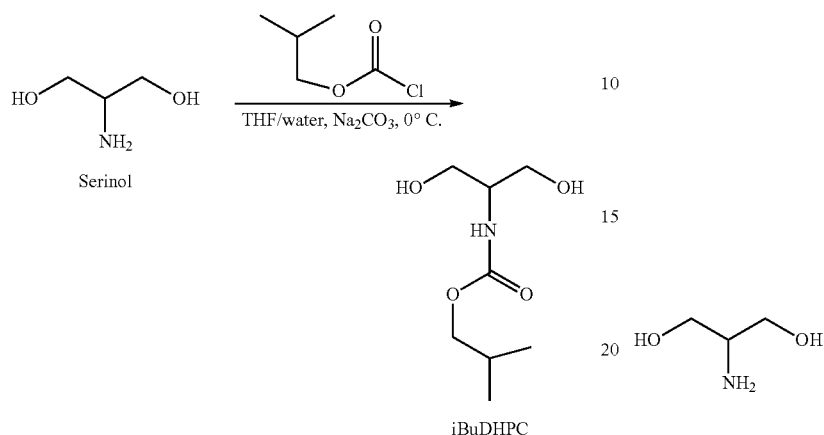

EXAMPLE 4

Ethyl 2-oxo-1,3-dioxan-5-yl-carbamate (EtODC) was prepared using the general procedure of Example 1.

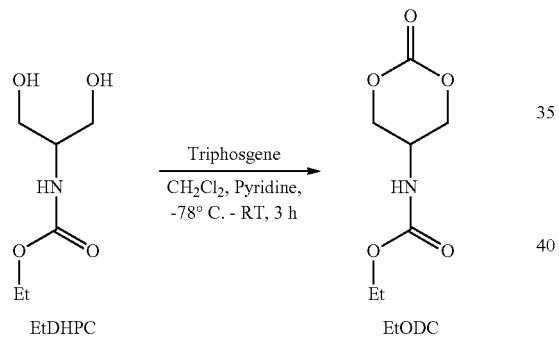

EXAMPLE 5

Isobutyl 2-oxo-1,3-dioxan-5-yl-carbamate (iBuODC) was prepared using the general procedure of Example 1.

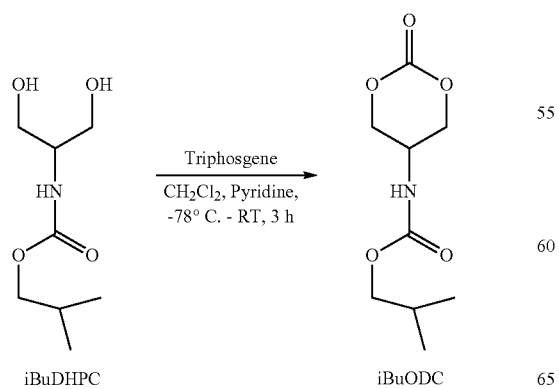

EXAMPLE 6

C5DHPA was prepared according to the following reaction.

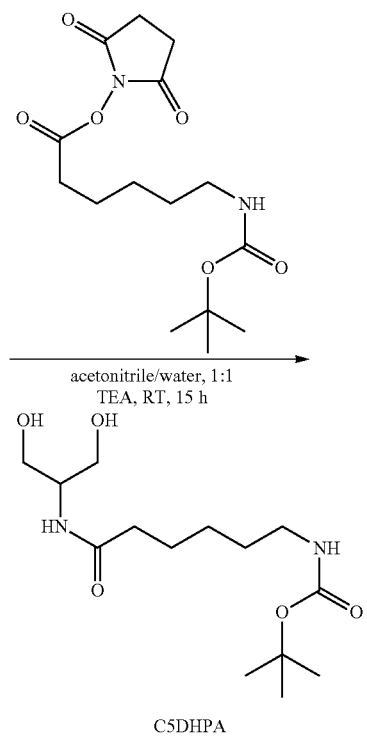

In a 500 mL round bottom flask with magnetic stir bar, 6-(Boc-amino)caproic acid N-succinimidyl ester (5.0 g, Sigma Aldrich (>98.0%)) and serinol (1.7 g) were dissolved in the mixture of DI water (125 mL) and acetonitrile (125 mL). About 20 drops of triethyl amine (TEA) were added to the reaction mixture and the reaction was allowed to proceed under nitrogen at room temperature (RT) for 15 hours. Another 100 mL of DI water was added to the reaction mixture and the product was extracted into ethyl acetate (6×200 mL). The final product, C5DHPA was a white solid (3.7 g, 79.8%).

EXAMPLE 7

C5ODA was prepared as follows.

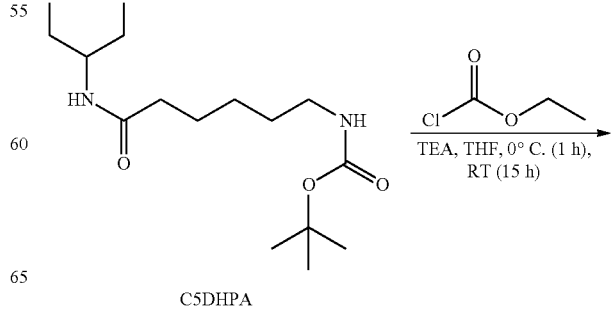

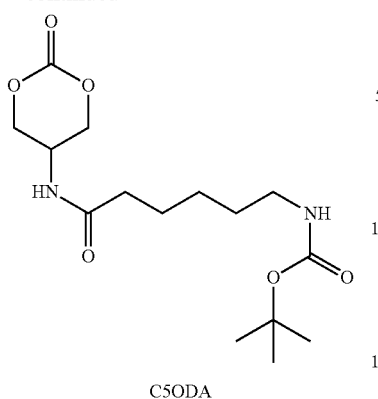

C5ODA

EXAMPLE 8

In a 500 mL round bottom flask with magnetic stir bar, under nitrogen atmosphere, C5DHPA (4.8 g, 18.3 mmol, 1.0 equivalent) and ethyl chloroformate (7.0 mL, 8.0 g, 73.7 mmol, 4.0 equivalents) were dissolved in THF (250 mL). The reaction mixture was allowed to equilibrate to ice-cold conditions for 30 minutes and TEA (10.2 mL, 7.4 g. 73.3 mmol, 4.0 equivalents) was added drop-wise (over 20 minutes) to the cold reaction mixture. After 1 hour the reaction mixture was allowed to warm up to room temperature, and the reaction was stirred for about 15 hours. Subsequently, the TEA.HCl salt was precipitated and removed by filtration, and the volatiles were removed under vacuum, resulting in a half-white waxy solid as the crude product. The crude product was further purified by recrystallization from tetrahydrofuran:diethyl ether (10:90 to 20:80 v/v) (100 mL) to give a white solid (2.4 g, 48%).

EXAMPLE 9

Preparation of TMCOBu

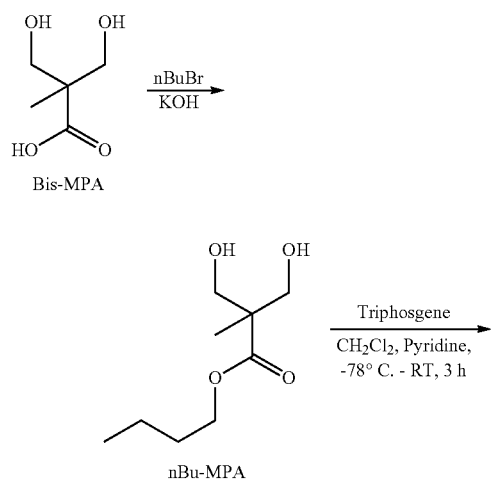

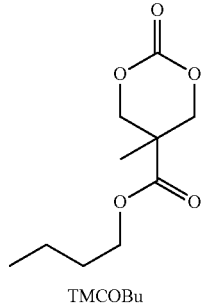

TMCOBu

A) In a 250 mL round bottom flask with magnetic stir bar, a mixture of KOH (85% purity, 14.5 g, 0.22 mol), bis(2-methylol)propionic acid (bis-MPA) (29.57 g, 0.22 mol) and DMF (150 mL) were heated to 100° C. for 1.5 hours. A homogenous solution was formed, and 1-bromobutane (22.0 mL, 0.2 mol) was added to the hot solution. Stirring was continued with heating for 16 hours and most of the DMF was removed under reduced pressure, to result in oily liquid, which was then dissolved in chloroform (300 mL). The organic solution was washed thrice with saturated brine (100 mL) and deionized water (100 mL) mixture. The combined organic layer was dried with $Na_2SO_4$ and the solvent removed in vacuo to result in the diol precursor, nBu-MPA as a pale oily liquid (20.6 g).

B) In a 500 mL round bottom flask with magnetic stir bar, nBu-MPA (20.6 g, 108 mmol) was dissolved in anhydrous dichloromethane (200 mL). Pyridine (50.0 mL, 619 mmol) was added and the solution was cooled in a dry ice-acetone bath (−78° C.). To this cooled reaction mixture, triphosgene (15.4 g, 51.9 mmol) solution (dissolved in 100 mL dichloromethane) was added dropwise over 1 hour. After 1 hour, from −78° C., the reaction mixture was allowed to warm up to room temperature, and after 2 hours, the reaction was quenched by adding saturated aqueous ammonium chloride solution (50 mL). The organic layer was washed twice with 1.0 N HCl (100 mL), followed by saturated $NaHCO_3$ (100 mL) and saturated NaCl (100 mL) and dried using $Na_2SO_4$. Removal of solvent in vacuo resulted in crude product TMCOBu (21.0 g), which was further purified by recrystallization from ethyl acetate.

EXAMPLE 10

Preparation of BnMPA

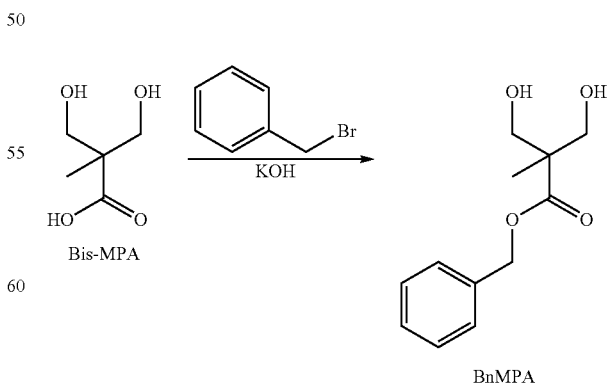

BnMPA was prepared according to the general procedure used in part A) above for the preparation of nBu-MPA, substituting bromobutane with benzyl bromide. The reaction mixture was stirred at 100° C. for 15 hours (yield 62%).

EXAMPLE 11

Synthesis of n-butyl 1,3-dihydroxypropan-2-yl-carbamate, (nBuDHPC)

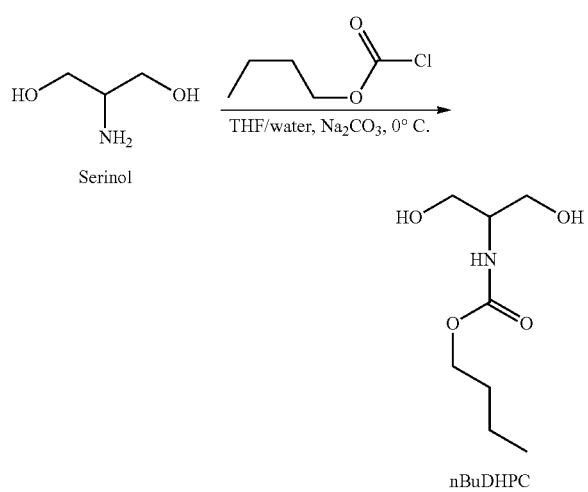

The general procedure described in Example 2 was followed using serinol and n-butyl chloroformate to prepare nBuDHPC.

EXAMPLE 12

Synthesis of n-butyl 2-oxo-1,3-dioxan-5-yl-carbamate (nBuODC)

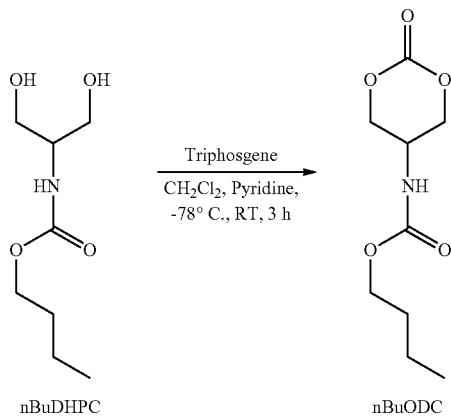

nBuODC was prepared using the general procedure of Example 1. Ring Opening Polymerization.

EXAMPLE 13

Preparation of protected polycarbonate PPC1, a homopolymer formed with tBuODC, or poly(tert-butyl 2-oxo-1,3-dioxan-5-yl-carbamate), is representative of ring opening polymerizations initiated with benzyl alcohol to prepare protected polycarbonate homopolymers and copolymers.

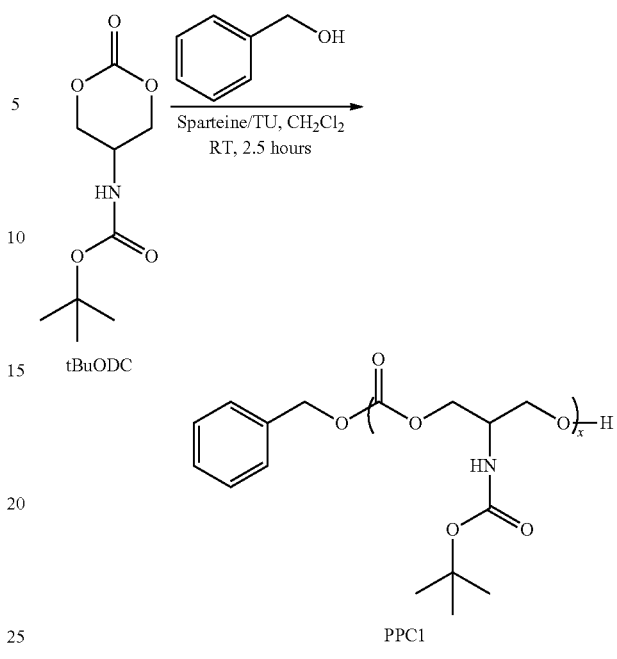

In a 7 mL vial containing a magnetic stir bar, in a glove box, tBuODC (532 mg, 2.447 mmol, 25.2 equivalents) and BzOH (10.0 microliters, 10.5 mg, 97.1 micromoles, 1.0 equivalents) and TU (38.0 mg, 103 micromoles, 1.06 equivalents) were dissolved in dichloromethane (5.0 mL). To this solution, (−)-sparteine (22.3 microliters, 22.7 mg, 97.0 micromoles, 1.0 equivalents) was added to initiate polymerization. The reaction mixture was allowed to stir at room temperature, and aliquots of samples were taken to monitor the monomer conversion and evolution of molecular weight by $^1$H NMR spectroscopy and size exclusion chromatography (SEC). After 4.0 hours, the reaction was quenched by the addition of 20 mg of benzoic acid. Dichloromethane was removed by evaporation. The crude product was dissolved in THF (<1 mL) and was precipitated into ice-cold methanol/DI-water mixture (50:50, 1×50 mL). The polycarbonate polymer was dried in a tared vial for 1 day to 2 days, until a constant sample mass was obtained as white powder.

EXAMPLE 14

Preparation of PPC2, poly(tert-butyl 2-oxo-1,3-dioxan-5-yl-carbamate-co-ethyl 2-oxo-1,3-dioxan-5-yl-carbamate)

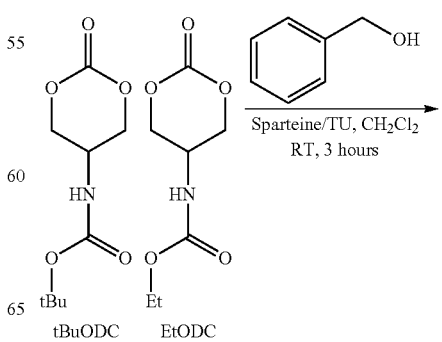

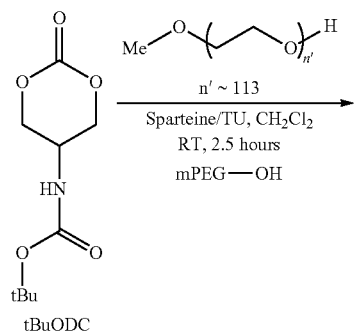

PPC2

In a 7 mL vial containing a magnetic stir bar, in a glove box, tBuODC (467 mg, 2.150 mmol, 22.1 equivalents), EtODC (56.3 mg, 0.298 mmol, 3.1 equivalents) and BzOH (10.0 microliters, 10.5 mg, 97.1 micromoles, 1.0 equivalent) and TU (36.1 mg, 97.5 micromoles, 1.0 equivalent) were dissolved in dichloromethane (5.0 mL). To this solution, (−)-sparteine (22.3 microliters, 22.7 mg, 97.0 micromole, 1.0 equivalent) was added to initiate polymerization. The reaction mixture was allowed to stir at room temperature, and aliquots of samples were taken to monitor the monomer conversion and evolution of molecular weight by $^1$H NMR spectroscopy and SEC. After 4 hours, the reaction was quenched by the addition of about 20 mg of benzoic acid. Dichloromethane was removed by evaporation. The crude product was dissolved in THF (1 mL), and then precipitated into ice-cold methanol/DI-water mixture (50:50, 1×50 mL). The polymer was dried in a tared vial for 1 day to 2 days, until a constant sample mass was obtained as white powder. The values of x and y are listed in Table 7 further below.

EXAMPLES 15 to 17

Preparation of PPC3 to PPC5, respectively. Using the general procedure of Example 14, various protected polycarbonate random copolymers were prepared by ROP of a mixture containing tBuODC (monomer 1) and EtODC (monomer 2), initiated by benzyl alcohol, each utilizing different amounts of monomer 1 and monomer 2 (Table 7).

EXAMPLE 18

Preparation of PPC6, block copolymer methoxy poly(ethylene glycol)-b-poly(tert-butyl 2-oxo-1,3-dioxan-5-ylcarbamate)

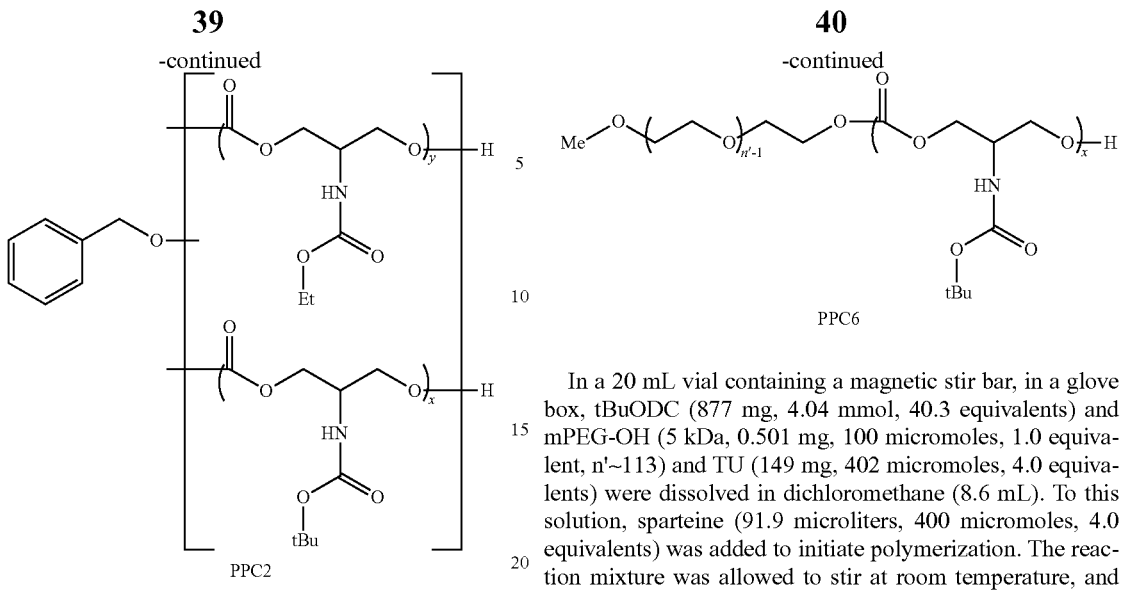

PPC6

In a 20 mL vial containing a magnetic stir bar, in a glove box, tBuODC (877 mg, 4.04 mmol, 40.3 equivalents) and mPEG-OH (5 kDa, 0.501 mg, 100 micromoles, 1.0 equivalent, n'~113) and TU (149 mg, 402 micromoles, 4.0 equivalents) were dissolved in dichloromethane (8.6 mL). To this solution, sparteine (91.9 microliters, 400 micromoles, 4.0 equivalents) was added to initiate polymerization. The reaction mixture was allowed to stir at room temperature, and aliquots of samples were taken to monitor the monomer conversion and evolution of molecular weight by $^1$H NMR spectroscopy and SEC. After about 4 hours, the reaction was quenched by the addition of about 100 mg of benzoic acid. Dichloromethane was removed by evaporation. The crude product was dissolved in THF (<3 mL) and then precipitated into ice-cold hexanes/diethyl ether mixture (50:50, 1×100 mL). The polymer PPC6 was dried in a tared vial for 1 day to 2 days, until a constant sample mass was obtained.

EXAMPLE 19

Preparation of PPC7, block copolymer methoxy poly(ethylene glycol)-b-poly(isobutyl 2-oxo-1,3-dioxan-5-ylcarbamate)

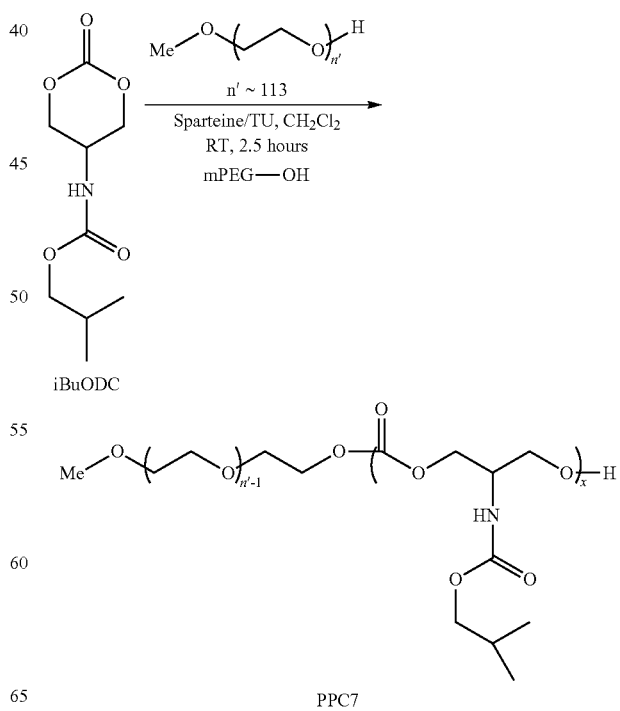

PPC7

The above block copolymer was prepared according to the general procedure of Example 18 using iBuODC and mPEG-OH (5 kDa).

EXAMPLES 20 and 21

PPC8 and PPC9, respectively. Using the general procedure of Example 18, two protected polycarbonate block copolymers were prepared by ROP of a mixture of tBuODC (monomer 1) and iBuODC (monomer 2) initiated by mono-methyl poly(ethylene glycol) (mPEG-OH, 5 kDa) as shown in the following reaction.

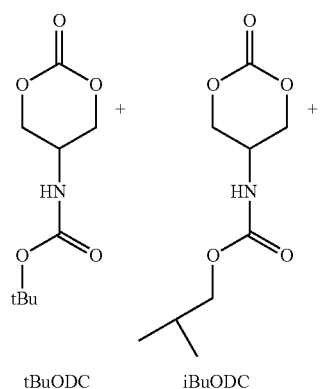

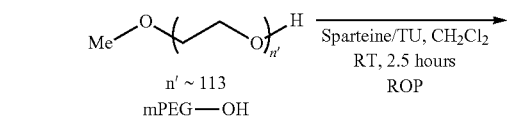

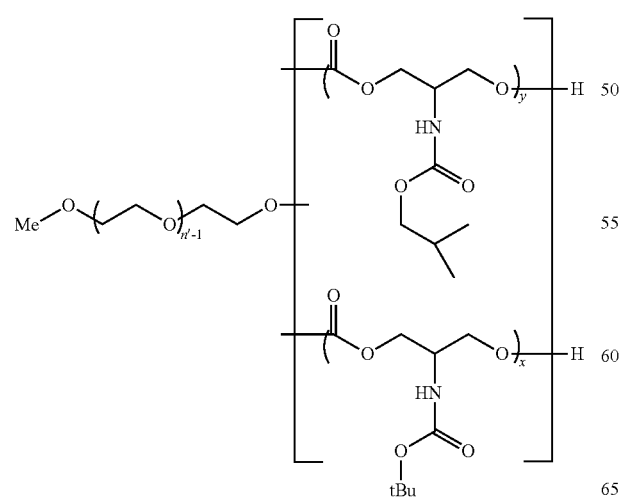

The block copolymers PPC8 and PPC9 differ by the amount of each monomer as listed in Table 7. The polycarbonate block of the block copolymer is a random copolymer.

Star Polymers

EXAMPLE 22

Preparation of 4-Arm Star Polymer PPC10

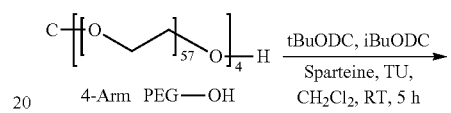

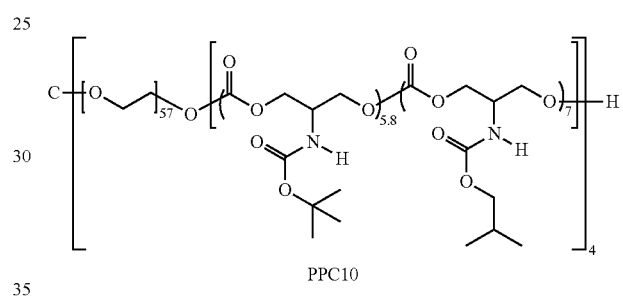

In a 7 mL vial containing a magnetic stir bar, in a glove box, tBuODC (87 mg, 401 micromoles, 41 equivalents), iBuODC (87 mg, 401 micromoles, 41 equivalents), TU (7.4 mg, 20 micromoles, 2.1 equivalents) and 4-Arm PEG-OH (10 kDa, 97 mg, 9.7 micromoles, 1.0 equivalent) were dissolved in dichloromethane (1.0 mL). To this solution, sparteine (4.6 microliters, 20 micromole, 2.1 equivalents) was added to initiate polymerization. The reaction mixture was allowed to stir at room temperature, and aliquots of samples were taken to monitor the monomer conversion and evolution of molecular weight by $^1$H NMR spectroscopy and SEC. After 5 hours, the reaction was quenched by the addition of about 10 mg of benzoic acid. Dichloromethane was removed by evaporation. The crude product was dissolved in THF (<1 mL) and was precipitated twice into ice-cold diethyl ether (2×50 mL). The polycarbonate polymer was dried in a tared vial for 1 day to 2 days, until a constant sample mass was obtained as white powder. $M_n$=21 kDa by NMR analysis, PDI=1.30. Each arm of PPC10 is a block copolymer comprising a first block of poly(ethylene oxide) and second block containing a random polycarbonate copolymer formed by the ring opening polymerization.

EXAMPLE 23

Preparation of ABA Triblock Copolymer PPC11

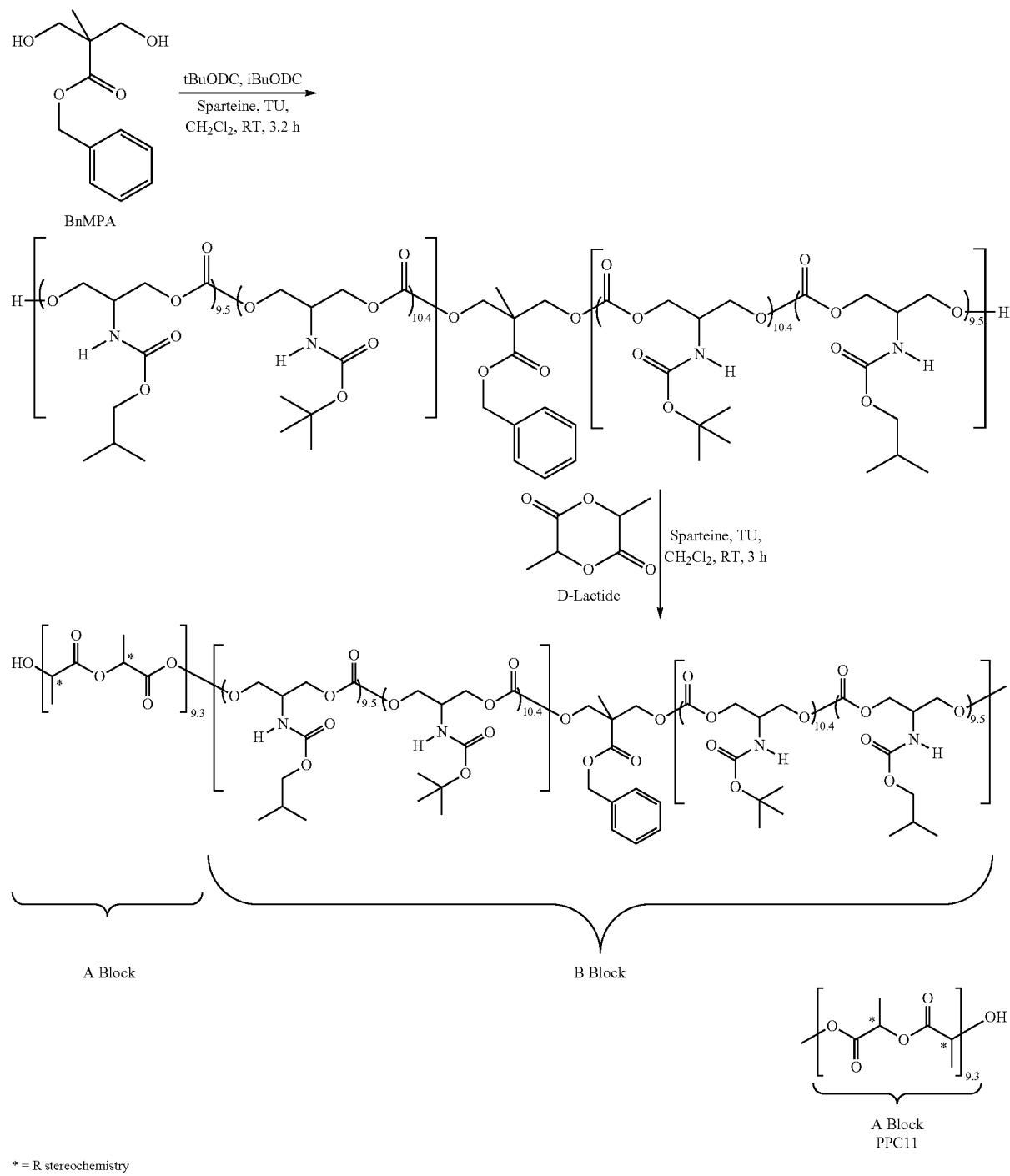

* = R stereochemistry

In a 7 mL vial containing a magnetic stir bar, in a glove box, tBuODC (88 mg, 405 micromoles, 18.2 equivalents), iBuODC (82 mg, 377 micromoles, 16.9 equivalents) and TU (13.8 mg, 37.3 micromoles, 1.7 equivalents) were dissolved in dichloromethane (1.0 mL). To this solution, BnMPA (5.0 mg in 100 microliters of DCM from 25 mg in 500 microliters stock solution; 22.3 micromoles, 1.0 equivalent) and sparteine (7.7 microliters, 33.5 micromoles, 1.5 equivalents) was added to initiate polymerization. The reaction mixture was allowed to stir at room temperature, and aliquots of samples were taken to monitor the monomer conversion and evolution of molecular weight by $^1$H NMR spectroscopy and SEC. After 3.2 hours (total monomer conversion>95%), the polymer was further chain extended by the addition of D-Lactide (DLA) monomer (60 mg, 416 micromoles, 18.7 equivalents). After additional 3 hours the reaction was quenched by the addition of about 20 mg of benzoic acid. Dichloromethane was removed by evaporation. The crude product was dissolved in THF (<1 mL) and was precipitated into ice-cold methanol/DI-water mixture (50:50, 1×50 mL). The polycarbonate polymer was dried in a tared vial for 1 day to 2 days, until a constant sample mass was obtained as white powder. $M_n$=11.5 kDa by NMR; PDI=1.30.

EXAMPLE 24

PPC12 was prepared using the general procedure of Example 13 using C5ODA and benzyl alcohol initiator. The reaction is shown below.

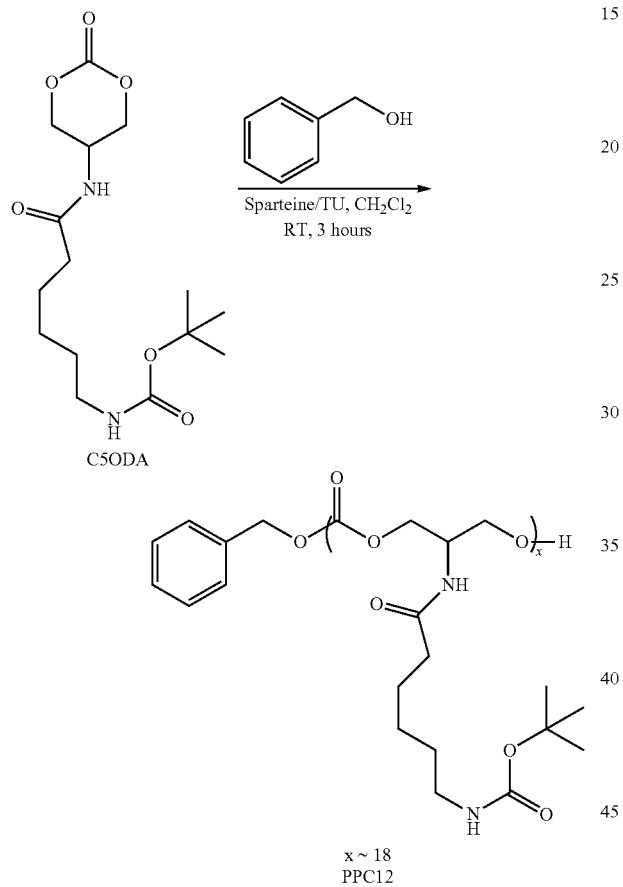

In a 7 mL vial containing a magnetic stir bar, in a glove box, C5ODA (161 mg, 0.487 mmol, 20.0 equivalents) BzOH (2.5 microliters, 2.6 mg, 24.3 micromoles, 1.0 equivalent) and TU (8.8 mg, 23.8 micromoles, 1.0 equivalent) were dissolved in dichloromethane (1.0 mL). To this solution, (−)-sparteine (5.6 microliters, 5.7 mg, 48.7 micromole, 1.0 equivalent) was added to initiate polymerization. The reaction mixture was allowed to stir at room temperature, and aliquots of samples were taken to monitor the monomer conversion and evolution of molecular weight by $^1$H NMR spectroscopy and SEC. After 3 hours, the reaction was quenched by the addition of about 20 mg of benzoic acid. The crude polymer was immediately used for the deprotection step, Example 39.

EXAMPLE 25

PPC13 was prepared using the general procedure of Example 24. In a 7 mL vial containing a magnetic stir bar, in a glove box, C5ODA (320 mg, 0.969 mmol, 20.0 equivalents) BzOH (5.0 microliters, 5.3 mg, 48.5 micromoles, 1.0 equivalent) and TU (18.2 mg, 49.1 micromoles, 1.0 equivalent) were dissolved in dichloromethane (2.0 mL). To this solution, (−)-sparteine (11.2 microliters, 11.4 mg, 48.7 micromole, 1.0 equivalent) was added to initiate polymerization. The reaction mixture was allowed to stir at room temperature, and aliquots of samples were taken to monitor the monomer conversion and evolution of molecular weight by $^1$H NMR spectroscopy and SEC. After 6 hours, the reaction was quenched by the addition of about 25 mg of benzoic acid. Crude polymers were immediately deprotected by using 10-20 equivalents of TFA (30-50% v/v) in DCM at RT for 1 hour. After deprotection, the polymers were precipitated twice into cold diethyl ether (50 mL) and after extensive drying (1-2 days) resulted in hygroscopic white powder. The crude polymer was immediately used for the deprotection step, Example 40.

EXAMPLE 26

PPC14 was prepared using the general procedure of Example 24. In a 7 mL vial containing a magnetic stir bar, in a glove box, C5ODA (320 mg, 0.969 mmol, 40.0 equivalents) BzOH (2.5 microliters, 2.6 mg, 24.3 micromoles, 1.0 equivalent) and TU (18.6 mg, 50.0 micromoles, 2.1 equivalents) were dissolved in dichloromethane (2.0 mL). To this solution, (−)-sparteine (11.2 microliters, 11.4 mg, 48.7 micromole, 2.0 equivalents) was added to initiate polymerization. The reaction mixture was allowed to stir at room temperature, and aliquots of samples were taken to monitor the monomer conversion and evolution of molecular weight by $^1$H NMR spectroscopy and SEC. After 6 hours, the reaction was quenched by the addition of about 25 mg of benzoic acid. The crude polymer was immediately used for the deprotection step, Example 41.

EXAMPLE 27

PPC15 was prepared according to the following reaction.

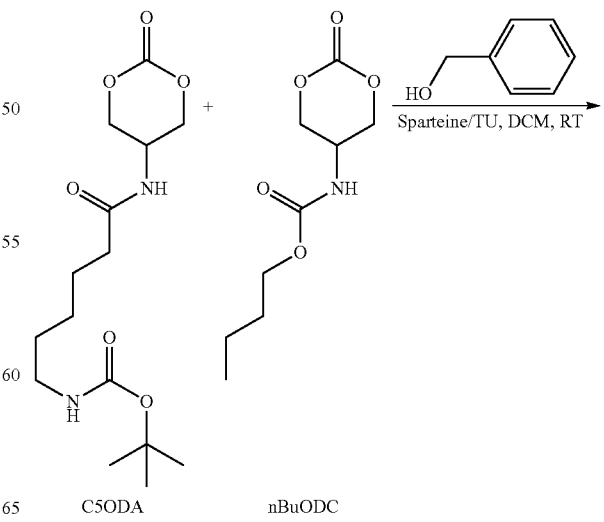

-continued

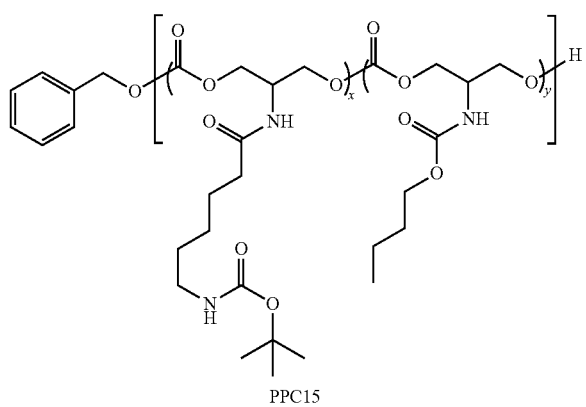

PPC15

In a 7 mL vial containing a magnetic stir bar, in a glove box, C5ODA (160 mg, 0.484 mmol, 10.0 equivalents) nBuODC (111 mg, 0.511 mmol, 10.5 equivalents), BzOH (5.0 microliters, 5.3 mg, 48.5 micromoles, 1.0 equivalent) and TU (18.0 mg, 48.6 micromoles, 1.0 equivalent) were dissolved in dichloromethane (2.0 mL). To this solution, (–)-sparteine (11.2 microliters, 11.4 mg, 48.7 micromole, 1.0 equivalent) was added to initiate polymerization. The reaction mixture was allowed to stir at room temperature, and aliquots of samples were taken to monitor the monomer conversion and evolution of molecular weight by $^1$H NMR spectroscopy and SEC. After 6 hours, the reaction was quenched by the addition of about 20 mg of benzoic acid. The crude polymer was immediately used for the deprotection step, Example 42.

EXAMPLE 28

PPC16 was prepared using the general procedure of Example 27. In a 7 mL vial containing a magnetic stir bar, in a glove box, C5ODA (233 mg, 0.705 mmol, 14.5 equivalents) nBuODC (63 mg, 0.290 mmol, 6.0 equivalents), BzOH (5.0 microliters, 5.3 mg, 48.5 micromoles, 1.0 equivalents) and TU (18.0 mg, 48.6 micromoles, 1.0 equivalent) were dissolved in dichloromethane (2.0 mL). To this solution, (–)-sparteine (11.2 microliters, 11.4 mg, 48.7 micromole, 1.0 equivalent) was added to initiate polymerization. The reaction mixture was allowed to stir at room temperature, and aliquots of samples were taken to monitor the monomer conversion and evolution of molecular weight by $^1$H NMR spectroscopy and SEC. After 3 hours, the reaction was quenched by the addition of about 20 mg of benzoic acid. The crude polymer was immediately used for the deprotection step, Example 43.

Table 7 which summarizes the composition and properties of the protected amine polymers, PPC1 to PPC16.

TABLE 7

| Example | Name | Initiator | Monomer 1 | Monomer 1 (mmol) | Monomer 2 | Monomer 2 (mmol) | Monomer 3 | Monomer 3 (mmol) | Mn (SEC)[a] Da | PDI[b] |
|---|---|---|---|---|---|---|---|---|---|---|
| 13 | PPC1 | BzOH | tBuODC | 2.447 | NA | NA | NA | NA | 6900 | 1.09 |
| 14 | PPC2 | BzOH | tBuODC | 2.150 | EtODC | 0.298 | NA | NA | 7000 | 1.09 |
| 15 | PPC3 | BzOH | tBuODC | 1.750 | EtODC | 0.707 | NA | NA | 7100 | 1.10 |
| 16 | PPC4 | BzOH | tBuODC | 1.280 | EtODC | 1.183 | NA | NA | 7300 | 1.10 |
| 17 | PPC5 | BzOH | tBuODC | 0.682 | EtODC | 1.786 | NA | NA | 7000 | 1.11 |
| 18 | PPC6 | mPEG-OH | tBuODC | 4.037 | NA | NA | NA | NA | 12500 | 1.20 |
| 19 | PPC7 | mPEG-OH | iBuODC | 4.093 | NA | NA | NA | NA | 8700 | 1.19 |
| 20 | PPC8 | mPEG-OH | tBuODC | 3.006 | iBuODC | 1.027 | NA | NA | 11100 | 1.10 |
| 21 | PPC9 | mPEG-OH | tBuODC | 2.030 | iBuODC | 2.187 | NA | NA | 10500 | 1.19 |
| 22 | PPC10 | 4-Arm PEG-OH | tBuODC | 0.401 | iBuODC | 0.401 | NA | NA | 21000 | 1.30 |
| 23 | PPC11 | BnMPA | tBuODC | 0.405 | iBuODC | 0.377 | DLA | 0.416 | 11500 | 1.30 |
| 24 | PPC12 | BzOH | C5ODA | 0.487 | NA | NA | NA | NA | 5100 | 1.32 |
| 25 | PPC13 | BzOH | C5ODA | 0.969 | NA | NA | NA | NA | 4600 | 1.36 |
| 26 | PPC14 | BzOH | C5ODA | 0.969 | NA | NA | NA | NA | 6700 | 1.43 |
| 27 | PPC15 | BzOH | C5ODA | 0.484 | nBuODC | 0.511 | NA | NA | 4000 | 1.35 |
| 28 | PPC16 | BzOH | C5ODA | 0.705 | nBuODC | 0.290 | NA | NA | 8000 | 1.29 |

[a]Mn was obtained from SEC, in THF using PS standards, before deprotection of tBoc-groups.

[b]Polydispersity index as determined by SEC in THF using PS standards, before deprotection of tBoc-groups.

Deprotection of tBoc-Protected Polymers

In the following deprotection examples, subscripts x' and y' of the structures of the amine polymers APC1 to APC14 were determined by NMR after the deprotection step. Number average molecular weight (Mn) of APC1 to APC14 are listed in Table 8 as determined by NMR.

EXAMPLE 30

Deprotection of PPC1 to Form APC1

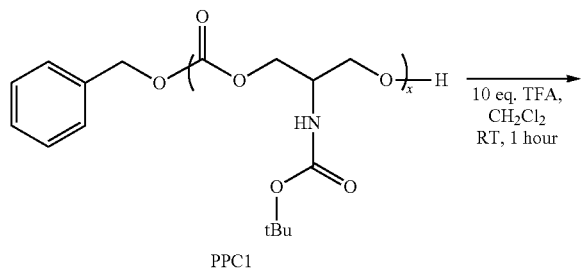

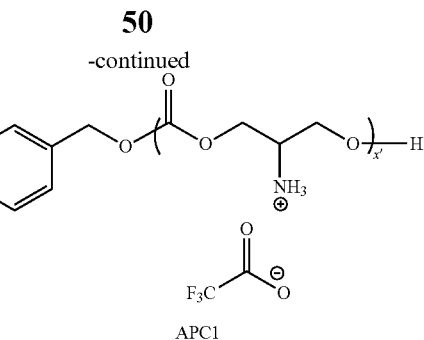

APC1

The following procedure is representative. The polymer PPC1 was dissolved in $CH_2Cl_2$, to which trifluoroacetic acid (TFA, about 10 equivalents with respect to tBoc groups) was added drop-wise and the reaction mixture was allowed to stir for 1 hour at room temperature, after which the solvent and excess TFA were removed by bubbling nitrogen gas through the solution. Residual volatiles were removed in vacuum to give amine polycarbonate APC1. Yields were generally over 90%.

EXAMPLES 31

Deprotection of PPC2 to form APC2. Using the procedure described above (Example 30), PPC2 (Example 14) was deprotected to form amine polycarbonate APC2, as shown below.

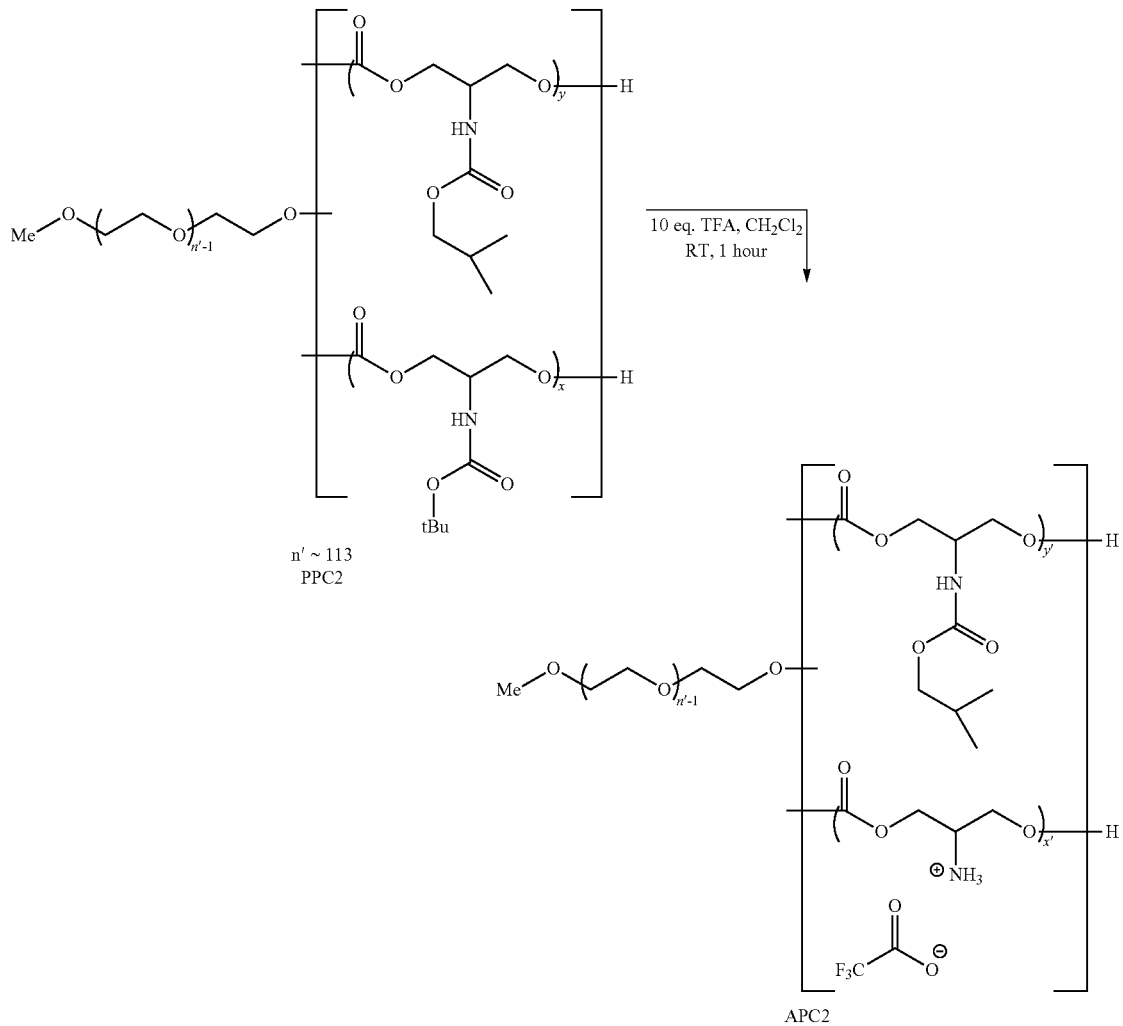

EXAMPLES 32, 33, and 34

APC3, APC4, and APC5 were prepared from protected polymers PPC3, PPC4, and PPC5 (Examples 15 to 17), respectively, using the general procedure of Example 30. APC3 to APC5 have the structure of APC2 above with different degrees of polymerization as indicated by the x' and y' values in Table 8.

EXAMPLE 35

APC6 (n'~113) was prepared from protected polymer PPC6 (Example 18) using the general procedure of Example 30 as shown below.

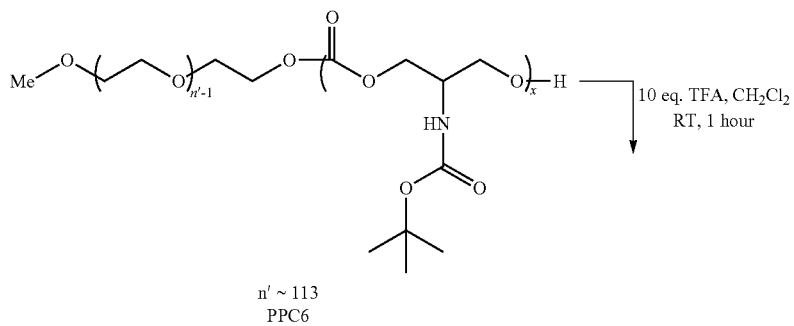

n' ~ 113
PPC6

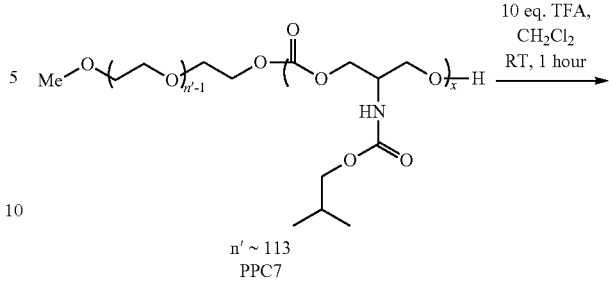

n' ~ 113
PPC7

No reaction

APC6

EXAMPLE 36

As a comparative example, the general procedure of Example 30 was used in an attempt to remove the isobutyl carbamate group of PPC7 as shown below. No reaction was observed. That is, trifluoroacetic acid did not deprotect the amine of the carbamate group.

EXAMPLES 37

APC8 was prepared from PPC8 (Example 20) using the general procedure of Example 30. APC8 has the structure shown below, with x' and y' listed in Table 8.

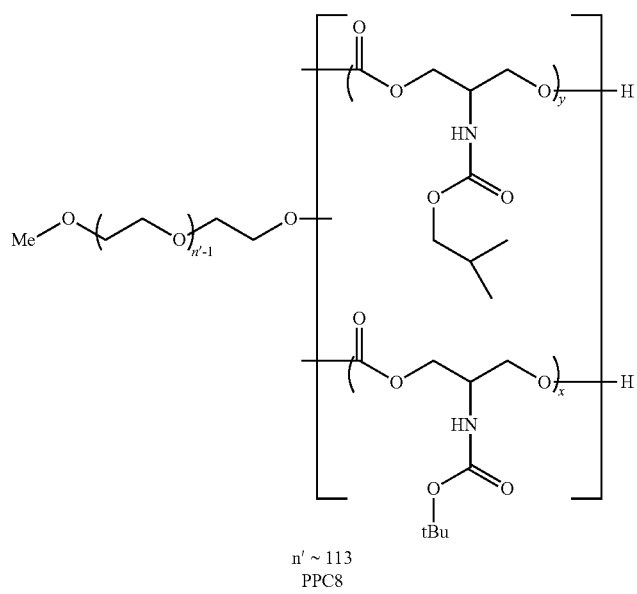
n' ~ 113
PPC8
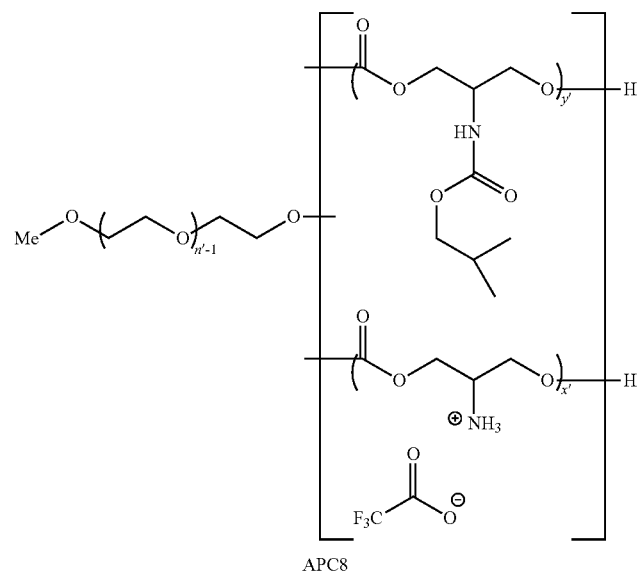
APC8
EXAMPLE 38
APC9 was prepared from PPC9 (Example 21) using the general procedure of Example 30. APC9 has the structure of APC8 shown above with different x' and y' listed in Table 8.
EXAMPLES 39 to 41
APC10 to APC12 were prepared from crude PPC12 to PPC14 (Examples 24 to 26), respectively, according to the following reaction.
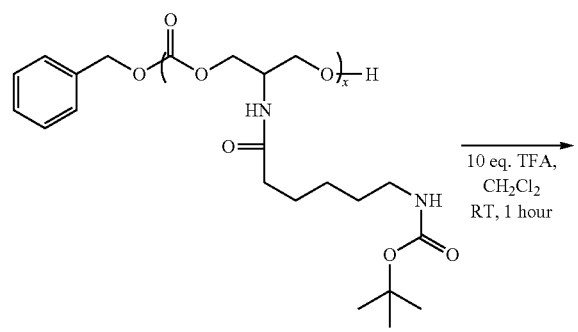
PPC12 x = 19
PPC13 x = 20
PPC14 x = 40

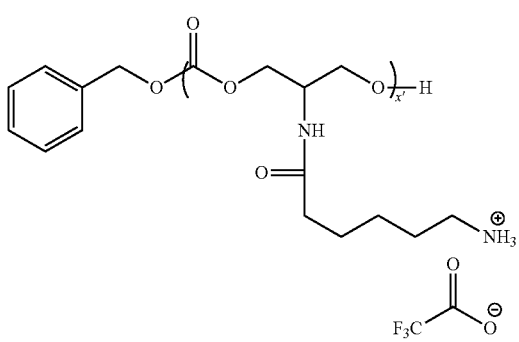

APC10 x' = 19
APC11 x' = 20
APC12 x' = 40

The following deprotection of PPC12 is representative. The crude polymer from Example 24 was deprotected immediately following the polymerization by using 10 to 20 equivalents of TFA (30-50% v/v) in DCM at RT for 1 hour. After deprotection, the polymer APC10 was precipitated twice into cold diethyl ether (50 mL) and after extensive drying (1-2 days) was obtained as a hygroscopic white powder.

APC11 and APC12 were prepared from PPC13 and PPC14, respectively, using the same procedure. APC10 to APC12 have the x' values listed in Table 8.

EXAMPLES 42 and 43

APC13 and APC14 were prepared from PPC15 and PPC16 (Examples 27 and 28), respectively, following the procedure of Example 39. The reaction is shown below.

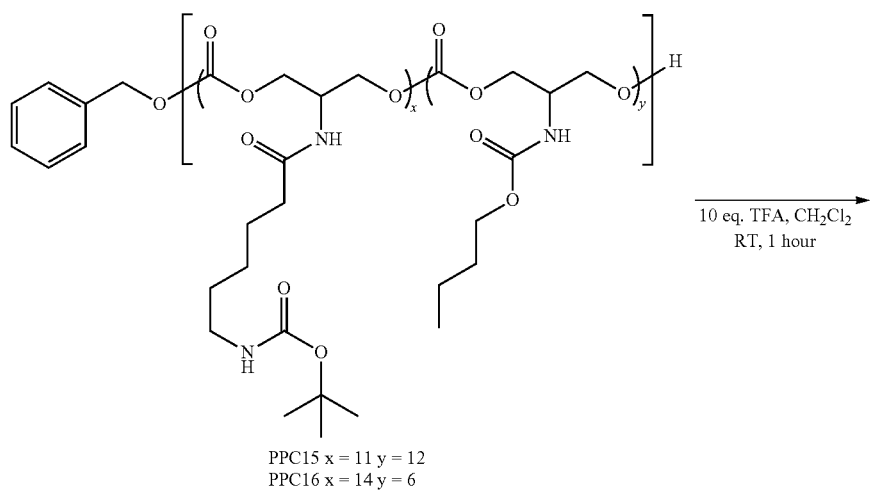

PPC15 x = 11 y = 12
PPC16 x = 14 y = 6

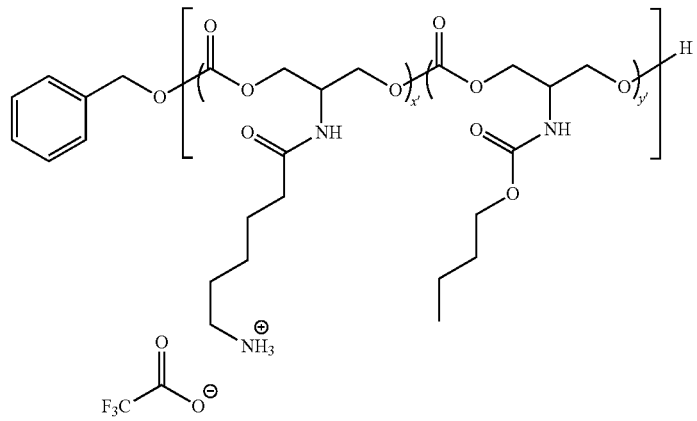

APC13 x' = 11 y' = 12
APC14 x' = 14 y' = 6

APC13 and APC14 have the x' and y' values listed in Table 8.

The properties of the amine polymers are summarized in Table 8.

TABLE 8

| Example | Name | Initiator | Monomer 1 | DP$^a$ (x') | Monomer 2 | DP$^a$ (y') | $M_n$ (NMR)$^b$, Da |
|---|---|---|---|---|---|---|---|
| 30 | APC1 | BzOH | tBuODC | 21 | — | — | 2600 |
| 31 | APC2 | BzOH | tBuODC | 19 | EtODC | 3 | 2900 |
| 32 | APC3 | BzOH | tBuODC | 16 | EtODC | 7 | 3300 |
| 33 | APC4 | BzOH | tBuODC | 13 | EtODC | 13 | 4000 |
| 34 | APC5 | BzOH | tBuODC | 6 | EtODC | 17 | 4100 |
| 35 | APC6 | mPEG-OH | tBuODC | 38 | — | — | 9500 |
| 36 (comp) | PPC7 | mPEG-OH | iBuODC | 30 | — | — | 11500 |
| 37 | APC8 | mPEG-OH | tBuODC | 30 | iBuODC | 10 | 10700 |
| 38 | APC9 | mPEG-OH | tBuODC | 21 | iBuODC | 21 | 12000 |
| 39 | APC10 | BzOH | C5ODA | 19 | NA | NA | 4600 |
| 40 | APC11 | BzOH | C5ODA | 20 | — | — | 4800 |
| 41 | APC12 | BzOH | C5ODA | 40 | — | — | 9400 |
| 42 | APC13 | BzOH | C5ODA | 11 | nBuODC | 12 | 5300 |
| 43 | APC14 | BzOH | C5ODA | 14 | nBuODC | 6 | 4600 |

$^a$DP was obtained from NMR.
$^b$Mn was obtained from NMR, after deprotection and without taking counter ion into consideration.

Antimicrobial Properties

The amine polymers were tested against *S. aureus*, *S. epidermidis*, *E. coli* and *C. albicans*. The results are listed in Table 9. A desirable MIC is less than 500 mg/L, preferably less than 250 mg/L.

10 microliter) were added to glass vials and air-dried to remove the acetone. Polymer solutions of varying concentrations were added to the pyrene at 1 mL each, and left to stand for 24 hours. The final pyrene concentration in each vial is $6.16 \times 10^{-7}$ M. The excitation spectra were scanned at wavelengths from 300 nm to 360 nm with an emission wavelength of 395 nm. Both the excitation and emission bandwidths were set at 2.5 nm. The intensity (peak height) ratio of $I_{337}/I_{334}$ from the excitation spectra was analyzed as a function of

TABLE 9

| | | | | | MIC (mg/L) | | | |
|---|---|---|---|---|---|---|---|---|
| Example | Name | Initiator | Monomer 1 | Monomer 2 | *E. coli* | *S. aureus* | *S. epidermis* | *C. albicans* |
| 30 | APC1 | BzOH | tBuODC | — | >2500$^c$ | >2500$^c$ | >2500$^c$ | 625$^e$ |
| 31 | APC2 | BzOH | tBuODC | EtODC | >2500$^c$ | >2500$^c$ | >2500$^c$ | 625$^e$ |
| 32 | APC3 | BzOH | tBuODC | EtODC | >2500$^c$ | >2500$^c$ | >2500$^c$ | 625$^e$ |
| 33 | APC4 | BzOH | tBuODC | EtODC | >2500$^c$ | >2500$^c$ | >2500$^c$ | 625$^e$ |
| 34 | APC5 | BzOH | tBuODC | EtODC | >2500$^c$ | >2500$^c$ | >2500$^c$ | 1250$^e$ |
| 35 | APC6 | mPEG-OH | tBuODC | — | ND | ND | ND | ND |
| 36 (comp) | PPC7 | mPEG-OH | iBuODC | — | ND | ND | ND | ND |
| 37 | APC8 | mPEG-OH | tBuODC | iBuODC | ND | ND | ND | ND |
| 38 | APC9 | mPEG-OH | tBuODC | iBuODC | ND | ND | ND | ND |
| 39 | APC10 | BzOH | C5ODA | — | 125$^d$ | 250$^d$ | ND | ND |
| 40 | APC11 | BzOH | C5ODA | — | 125$^d$ | 250$^d$ | ND | >1000$^e$ |
| 41 | APC12 | BzOH | C5ODA | — | 62.5$^d$ | 500$^d$ | ND | >1000$^e$ |
| 42 | APC13 | BzOH | C5ODA | nBuODC | 30$^d$ | 30$^d$ | ND | 250$^e$ |
| 43 | APC14 | BzOH | C5ODA | nBuODC | 30$^d$ | 62.5$^d$ | ND | ND |

$^a$DP was obtained from NMR.
$^b$Mn was obtained from NMR, after deprotection and without taking counter ion into consideration.
$^c$tryptic soy broth (T-SB);
$^d$Mueller Hinton broth (M-HB);
$^e$Yeast Mould broth
ND—Not determined Critical Micelle Concentration. Fluorescence Measurements The critical micelle concentrations (CMCs) of the polymers in deionized water were determined by fluorescence spectroscopy using pyrene as the probe. The fluorescence spectra were recorded by an LS 50B luminescence spectrometer (Perkin Elmer, U.S.A.) at 25° C. The polymer samples were equilibrated for 10 minutes before taking measurements. Aliquots of pyrene in acetone solution ($6.16 \times 10^{0.5}$ M, polymer concentration. The CMC was taken at the point of intersection between the tangent to the curve at the inflection and tangent of the data points at low concentrations.

Aqueous Encapsulation of Diclofenac (DCF) and Penicillin G (PenG) into Nanoparticles Amine polymer (10 mg) was dissolved in 1 mL of HPLC water via sonication. Next, 3 mg of the drug (either DCF or PenG) was dissolved in 9 mL of HPLC water in a separate vial. The polymer was then added to the drug and stirred at 500 rpm for 5 minutes. The mixture was then left to stand at room temperature for 5 hours. Unencapsulated drug was then removed via membrane ultrafiltration (Vivaspin MWCO 10 kDa, GE Healthcare, U.S.A.). At the end of the process, the resulting nanoparticle solution was then centrifuged at 4000 rpm for 5 min to remove large aggregates, and then transferred to a fresh vial. The micelles were characterized with respect to their size using a Zetasizer with dynamic light scattering capability (scattering angle: 90°) and equipped with a He—Ne laser beam at 658 nm (Malvern Instruments Zetasizer Nano ZS, U.K.).

Drug Loading Measurements

To determine the encapsulation efficiency and drug loading level, the drug-loaded nanoparticles were lyophilized and redissolved in 4 mL mobile phase. For DCF, the mobile phase consisted of acetonitrile/0.0025 M sodium acetate (65:35% v/v) adjusted to pH 4.0 with glacial acetic acid. The mobile phase for PenG was acetonitrile/0.025 M potassium phosphate (80:20% v/v) adjusted to pH 4.0 with phosphoric acid. The drug content was analyzed using high performance liquid chromatography (HPLC, Waters 996 PDA) at 276 nm and 204 nm UV wavelength for DCF and PenG respectively. Drug loading level in the nanoparticles was calculated according to the ratio of the amount of encapsulated drug to the total mass of the nanoparticles. The drug encapsulation efficiency was determined based on the ratio of the amount of drug successfully encapsulated into the nanoparticles to the amount of drug initially added during the micelle fabrication process.

In vitro DCF Release

Release of DCF from the DCF-loaded nanoparticles was studied using the dialysis method. 9 mL of DCF-loaded nanoparticles were transferred to a dialysis membrane tube with MWCO of 1 kDa (Spectrum Laboratories, U.S.A.) and dialysed against 40 mL of either PBS (pH 7.4) or 20 mM sodium acetate/acetic acid buffer (pH 5.6) solution. The set-up was kept shaking on an orbital shaker at 100 rpm at 37° C. At designated time intervals, 1 mL of the release medium was removed and replaced with fresh medium. The amount of DCF released into the medium was analyzed using HPLC at 276 nm as described above.

Minimal Inhibitory Concentration (MIC) Determination

Bacteria (*S. aureus*, *S. epidermis* and *E. coli*) and Yeast (*C. albicans*) obtained from ATCC were reconstituted from its lyophilized form according to the manufacturer's protocol. Bacterial samples were cultured in tryptic soy broth (T-SB) or Mueller Hinton broth (M-HB) solution at 37° C., and yeast cells were cultured in YMB at room temperature under constant shaking of 100 rpm. The MICs of the polymers were measured using the broth microdilution method. Briefly, 100 microliters of the respect broth medium containing a polymer at various concentrations (15.6, 31.3, 62.5, 125, 250, 500, 1000, 2000 mg/L) was placed into each well of a 96-well tissue culture plate. An equal volume of microbial suspension ($3\times10^5$ CFU/mL) was added into each well. Prior to mixing, the microbial sample was first inoculated overnight to enter its log growth phase. The concentration of microbial solution was adjusted to give an initial optical density (O.D.) reading of approximately 0.07 at 600 nm wavelength on a microplate reader (TECAN, Switzerland), which corresponds to the concentration of Mc Farland 1 solution ($3\times10^8$ CFU/mL), the microbial solution was further diluted by 1000 times to achieve an initial loading of $3\times10^5$ CFU/mL. The bacterial samples were kept in an incubator at 37° C. for 18 hours, while the Yeast samples were kept at room temperature for 42 hours under constant shaking of 100 rpm. The MIC was taken as the concentration of the polymer at which no microbial growth was observed with unaided eyes and the microplate reader at the end of the respect incubation time. Broth containing microbial cells alone was used as negative control, and each test was carried out in 6 replicates.

Cytotoxicity Study Using MTT Assay

Human dermal fibroblasts (HDF) were seeded onto 96-well plates at a density of $1.0\times10^4$ cells per well, and cultivated in 100 microliters of growth medium. The plates were incubated at 37° C. overnight to reach 70%-80% confluency before treatment. Polymer solutions of various concentrations were prepared. When the desired cell confluency was reached, the spent growth medium was removed from each well and replaced with 100 microliters of the pre-prepared solution and returned to the incubator. After 2 days of incubation, the culture medium was removed and 10 microliters of MTT solution was added together with 100 microliters of fresh medium. The plates were then incubated further for 3 hours. The growth medium and excess MTT in each well were then removed. 150 microliters of DMSO was then added to each well to dissolve the internalized purple formazan crystals. An aliquot of 100 microliters was taken from each well and transferred to a new 96-well plate. The plates were then assayed at 550 nm and reference wavelength of 690 nm using a microplate reader (TECAN, Switzerland). The absorbance readings of the formazan crystals were taken to be those at 550 nm subtracted by those at 690 nm. The results were expressed as a percentage of the absorbance of the control cells that did not receive any treatment.

Haemolysis Assay 100 microliters of rat red blood cell suspension in PBS (4% in volume) was placed in each well of 96-well plates, and 100 microliters of polymer solution were added to each well. The plates were incubated for one hour at 37° C. The cell suspensions were taken out and centrifuged at 1000 rpm for 5 minutes. Aliquots (100 microliters) of supernatant were transferred to 96-well plates, and hemoglobin release was monitored at 576 nm using a microplate reader (TECAN, Switzerland). The red blood cell suspension in PBS was used as negative control. Absorbance of wells with red blood cells lysed with 0.1% Triton X-100 was taken as 100% haemolysis. Percentage of haemolysis was calculated using the following equation (O.D.=optical density): Haemolysis (%)= $[(O.D._{576nm(polymer\ solution)} - O.D._{576nm(PBS)}) / (O.D._{576nm(0.1\%\ TRITON\ X-100)} - O.D._{576nm(PBS)})] \times 100$.

Shelf-Life Stability.

The size of freshly prepared DCF-loaded nanoparticles in de-ionized water was monitored at 22° C. for 30 days. After initial size measurements, the samples were stored under their respective storage conditions. At the designated time intervals, they were placed at room temperature for 0.5 hours to allow temperature equilibration before being analyzed directly in the sample tubes.

APC1 to APC5 were not loaded with drug because they were too hydrophilic, which causes undesirably high MIC and nanoparticles having a large hydrodynamic diameter. Also, non-charged amine polymer PPC7 was not loaded with anionic drug due to the lack of ionic binding sites in PPC7.

Table 10 summarizes the properties of the drug loaded nanoparticles obtained with the amine polymers.

TABLE 10

| Ex. | Name | Drug | Dh$^a$ (nm) | PDI | CMC$^b$ (mg/L) | Drug Loading Level (wt. %) | Drug Loading Efficieny (wt. %) |
|---|---|---|---|---|---|---|---|
| 44 | PPC7 | None | ND | ND | 3 | ND | ND |
| 45 | APC6 | DCF | 288/168 | 1.00/0.94 | 630 | 5.3 ± 1.0 | 1.6 ± 0.6 |
| 46 | APC8 | DCF | 233/212 | 0.24/0.23 | 200 | 16.8 ± 4.1 | 3.3 ± 0.5 |
| 47 | APC9 | DCF | 192/135 | 0.43/0.16 | 16 | 28.6 ± 0.7 | 46.2 ± 6.6 |
| 48 | APC9 | PenG | 192/84 | 0.43/0.15 | 16 | 16.2 ± 1.6 | 26.2 ± 0.3 |
| 49 | APC10 | ND | ND | ND | ND | ND | ND |

* Polymer insoluble
$^a$Hydrodynamic diameter and polydispersity index (PDI) of blank/drug-loaded micelles in water by dynamic light scattering.
$^b$Polymer alone
ND = not determined Critical Micelle Concentration (CMC) Determination There is a tendency for amphiphilic copolymers to self-associate in aqueous solution to form micellar structures, as demonstrated by the existence of their critical micelle concentrations. Table 10 lists the CMC values of the polymers in DI water, ranging from 3 to 630 mg/L. The vast range of CMC values indicates that the micellar structure is highly dependent on the hydrophobic-to-hydrophilic balance of the copolymers, with lower CMC values for polymers that have higher hydrophobic content.

Aqueous Encapsulation of Diclofenac (DCF) and Penicillin G (PenG) into Nanoparticles.

Diclofenac (DCF) and Penicillin G (PenG) were directly encapsulated into the nanoparticles without the use of organic solvents. The nanoparticles were characterized according to their size and drug loading capacities (Table 10). Ionic interactions between the cationic amine polymers and anionic carboxy group of DCF and PenG led to high drug loading level and encapsulation efficiency. The encapsulation of PenG into the nanoparticles also resulted in more tightly packed structures as indicated by the significant reduction in size and polydispersity of the DCF and PenG-loaded nanoparticles as compared to the blank nanoparticles. As shown in Table 10, the micelles before loading had an average hydrodynamic diameter in a range of 192 nm to 288 nm, inclusive. The loaded nanoparticles had an average hydrodynamic diameter in a range of 80 nm to 168 nm, inclusive.

In vitro DCF Release.

Figure 2:
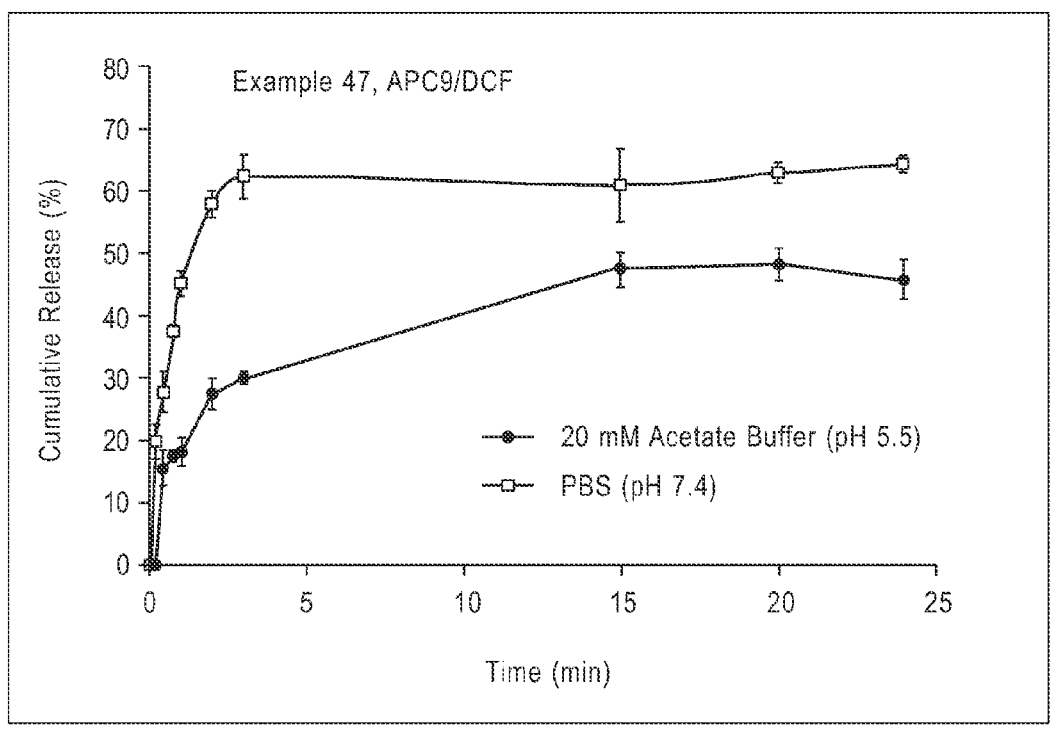
FIG. 2 is a graph showing pH-dependent release of diclofenac DCF from the loaded nanoparticles of Example 47 (amine polymer APC9 loaded with DCF), monitored for 24 hours at 37° C. in two different buffered solutions: PBS (pH 7.4) and 20 mM sodium acetate/acetic acid buffer (pH 5.6) solution.

The in vitro release of DCF from the nanoparticles of Example 47 (APC9/DCF) was monitored for 24 hours at 37° C. in two different buffered solutions (FIG. 2, graph)—PBS (pH 7.4) or 20 mM sodium acetate/acetic acid buffer (pH 5.6) solution. Comparing the drug release profiles at the two pHs shows that the release of DCF from the nanoparticles at pH 7.4 was significantly faster than at pH 5.6 with approximately 30% higher amount of DCF released. The increase in release rate at the higher pH was likely due to the deprotonation of the cationic amine polymer *—NH$_3^+$ group, which resulted in weaker binding of the anionic drug.

Antimicrobial Activity Results

The antimicrobial activity of the loaded nanoparticles fabricated from deprotected polymer APC9 was evaluated with respect to their corresponding bacteriostatic inhibitory concentrations, indicated by the MIC. APC9 itself displayed no inhibition on S. aureus proliferation while the PenG-loaded APC9 nanoparticles have a MIC of about 0.05 mg/L equivalent of PenG. This is approximately 5 times that of the free PenG (MIC about 0.01 mg/L). Further, APC9 polymer and the PenG-loaded APC9 nanoparticles had almost negligible hemolytic properties even at 200-times the eqv. polymer and PenG concentration (~2% hemolysis). APC6 and APC8 were not used to load PenG as they have high CMCs, which indicate a potential stability issue after intravenous injection.

Figure 3:
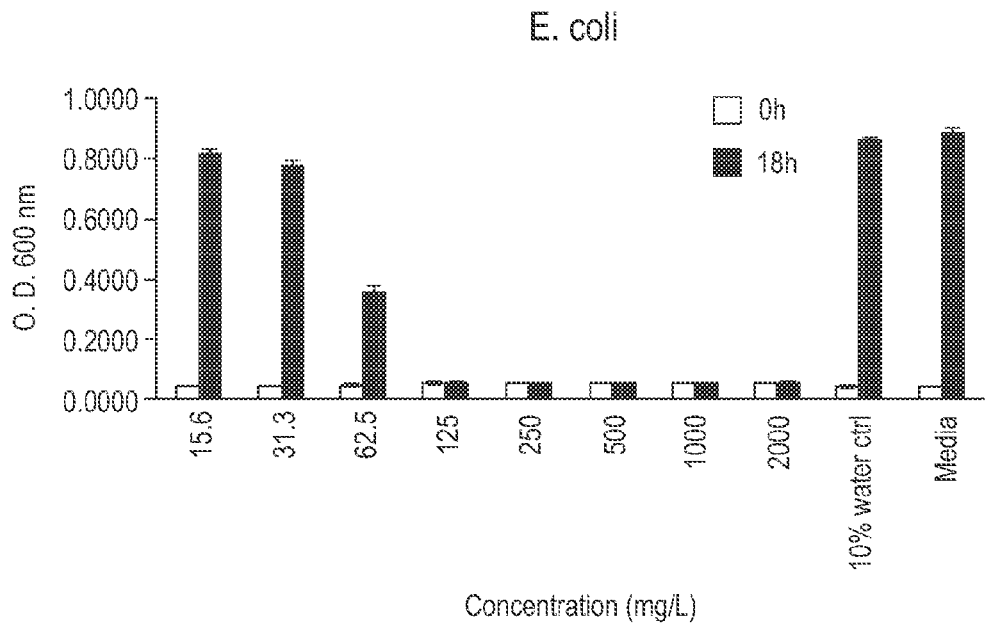
FIG. 3 is a bar graph demonstrating antimicrobial activity of APC10 (no drug added) against *Escherichia. coli* (*E. coli*). The minimum inhibitory concentration (MIC) was 125 mg/L.
Figure 4:
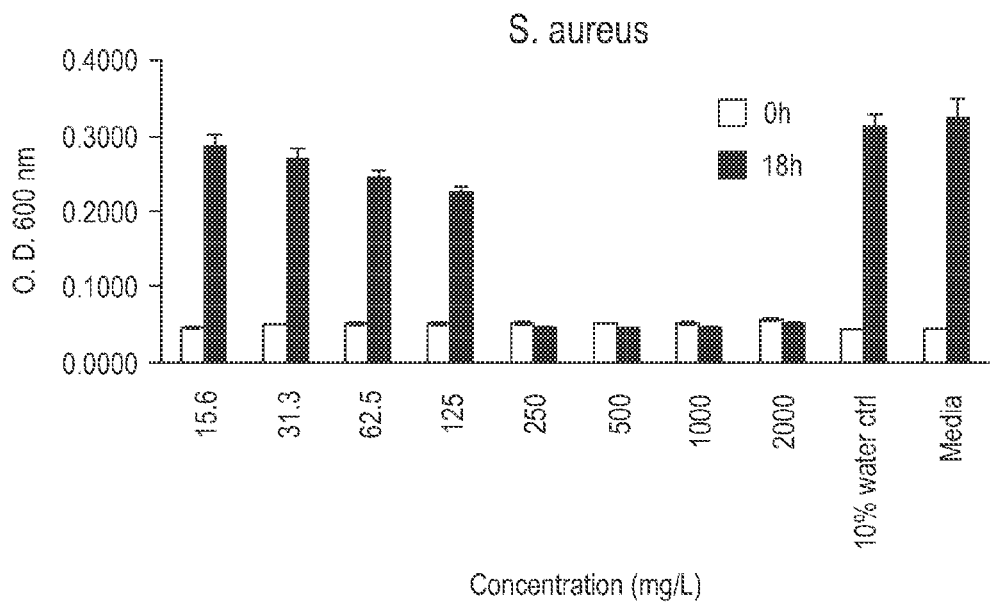
FIG. 4 is a bar graph demonstrating antimicrobial activity of APC10 (no drug added) against *Staphylococcus aureus* (*S. aureus*). The minimum inhibitory concentration (MIC) was 250 mg/L.

The homopolymer APC10 was highly active against E. coli (MIC 125 mg/L) and S. aureus (MIC 250 mg/L) without anionic drug added (FIGS. 3 and 4, respectively).

Effect of Polymers on Human Dermal Fibroblasts.

Figure 5:
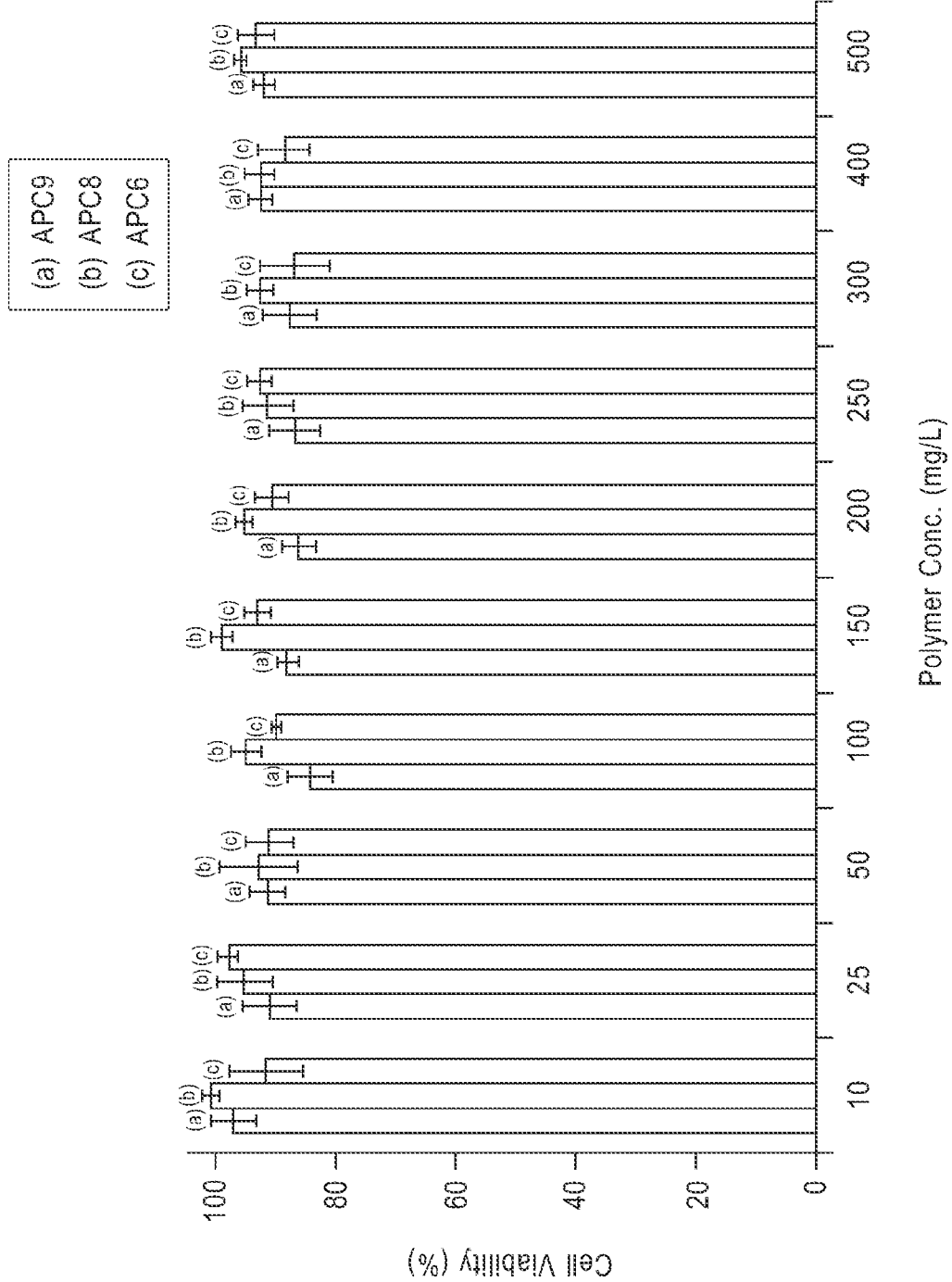
FIG. 5 is a bar graph demonstrating the non-cytotoxicity of polymers APC9, APC8, and APC25 labeled (a), (b), and (c), respectively, against human dermal fibroblasts (HDF). Cell viability remains high at >80% for concentrations up to 500 mg/L.

Polymers APC9, APC8 and APC6 were tested for toxicity against human dermal fibroblasts (HDF). Polymer APC7 was not tested as it is insoluble in water. As shown in the bar graph of FIG. 5 (APC9, APC8 and APC6 are labeled (a), (b), and (c), respectively) none of the polymers showed significant cytotoxicity against HDF cells. The HDF cell viability remained high at >80% for concentrations up to 500 mg/L.

Shelf-Life Stability Results.

Figure 6:
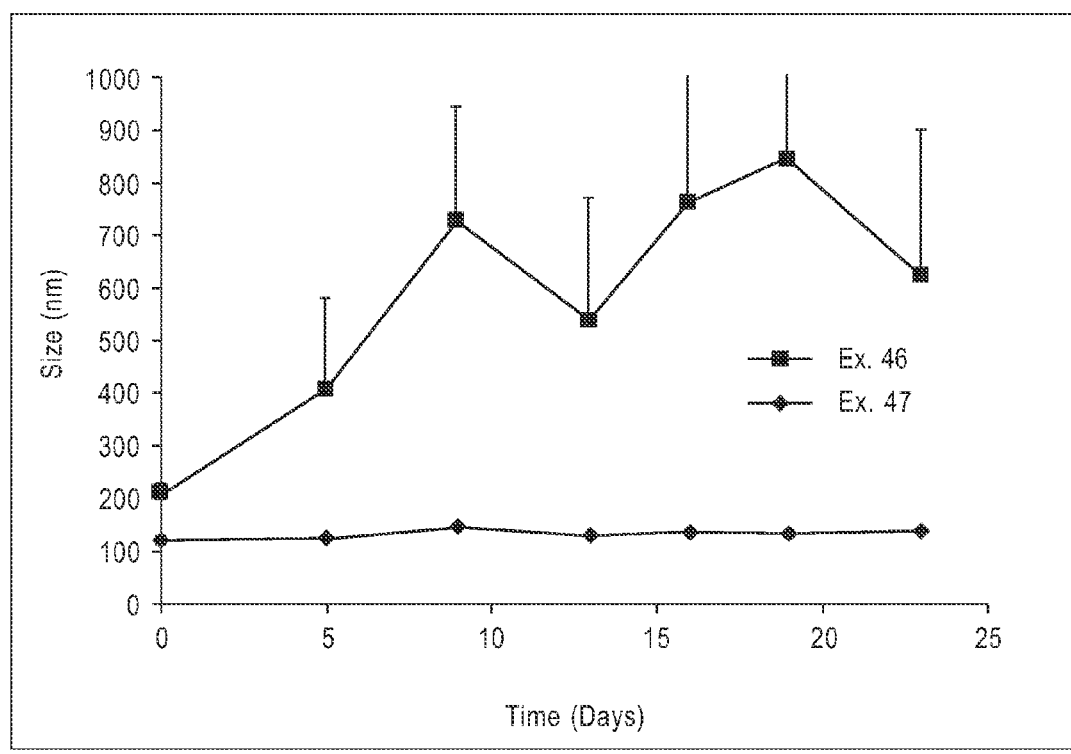
FIG. 6 is graph plotting particle size as a function of time for DCF-loaded nanoparticles of Examples 46 and 47 kept at 22° C. for 30 days.

DCF-loaded nanoparticles of Examples 46 and 47 fabricated from deprotected polymer APC8 and APC9, respectively, were tested for shelf-life stability by monitoring the change in particle size at 22° C. for 30 days (FIG. 6, graph). From FIG. 6, loaded nanoparticles of APC8, having a higher hydrophilic content, showed weaker particle size stability compared to loaded nanoparticles made from APC9. APC8 loaded nanoparticles showed a 5-fold increase in particle size (from 212 nm to 978 nm) over a 30-day period. Large fluctuations in the particle size were observed as the PDI was increased from 0.23 to 1. By comparison, loaded nanoparticles prepared from deprotected polymer APC9 were highly stable, showing negligible change in particle size and PDI (size ~125 nm, PDI ~0.1) over a 30 day period.

Conclusion

Aliphatic cyclic carbonate monomer containing protected primary amine functionality based on serinol has been prepared and this monomer can be either homo polymerized or copolymerized with other carbonate monomers. Upon selective deprotection of tBoc groups, these cationic polymers were used to encapsulate anionic drugs such as beta-lactam class of antibiotics (penicillin G sodium salt) and NSAID class of pain killers (diclofenac sodium salt). Apart from drug delivery applications, these materials have utility in the formation of inter-polyelectrolyte complex micelles and additional functional materials. APC9 was the most effective amine polymer for forming an antimicrobial composition with an anionic drug. The trifluoroacetate counterion of APC9 can be replaced with any suitable counterion X$^-$, and x' and y' of the above described APC9 structure can be 10 or more, and more particularly 20 or more. The poly(ethylene oxide) chain can have n' equal to 50 or more, more particularly 100 to 150, or an Mn of 1000 to 5000 Da.

In addition, each of the homopolymers APC10 to APC12, having a degree of polymerization of 19 to 40, was a highly effective antimicrobial agent alone against E. coli and S. aureus. Linear random copolymers APC13 and APC14, having a degree of polymerization of 23 and 20, respectively, were the most effective against E. coli and S. aureus.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. An antimicrobial composition, comprising:
an anionic drug; and
an amine polymer comprising a first repeat unit of formula (2):

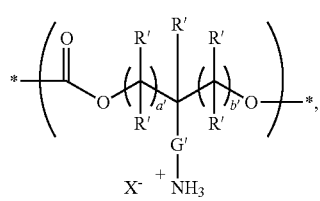

wherein
a' is an integer equal to 1 or 2,
b' is an integer equal to 1 or 2,
each R' is an independent monovalent radical selected from the group consisting of hydrogen, methyl, and ethyl,
G' is a divalent linking group comprising i) at least one carbon and ii) a nitrogen bonded to the backbone of the amine polymer,
$X^-$ is a negatively charged counterion, and
the drug and the amine polymer are bound by noncovalent interactions.

2. The composition of claim 1, wherein a' is 1 and b' is 1.

3. The composition of claim 1, wherein the amine polymer has a minimum inhibitory concentration (MIC) of more than 0 mg/L and less than 200 mg/L against a microbe.

4. The composition of claim 1, wherein the amine polymer has no repeat unit comprising a quaternary amine group.

5. The composition of claim 1, wherein the amine polymer is a polycarbonate and/or a polyestercarbonate.

6. The composition of claim 1, wherein the amine polymer is a diblock copolymer.

7. The composition of claim 1, wherein the amine polymer is a triblock copolymer.

8. The composition of claim 1, wherein the amine polymer is a star polymer comprising 6 or more independent block copolymer arms, wherein each of the arms comprises a first block comprising a poly(alkylene oxide) backbone linked to a second block comprising the first repeat unit, and the first block is linked by an end group to a covalently crosslinked microgel core of the star polymer.

9. The composition of claim 1, wherein the amine polymer is a pendant group of a covalently crosslinked hydrogel.

10. The composition of claim 1, wherein the drug is diclofenac (DCF).

11. The composition of claim 1, wherein the drug is penicillin G (PenG).

12. The composition of claim 1, wherein the amine polymer has the structure:

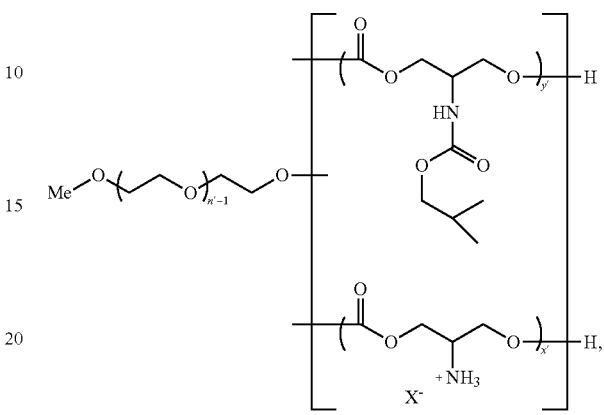

wherein $X^-$ is an negatively charged counterion, n' is 50 or more, x' is 10 or more, and y' is 10 or more.

13. An antimicrobial amine polymer, comprising:
a first repeat unit of formula (4):

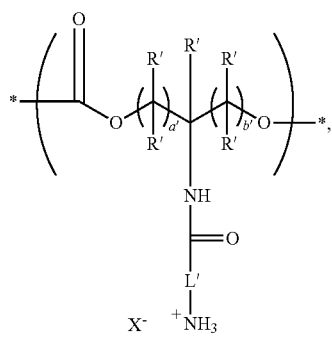

wherein
a' is an integer equal to 1 or 2,
b' is an integer equal to 1 or 2,
each R' is an independent monovalent radical selected from the group consisting of hydrogen, methyl, and ethyl,
L' is a divalent linking group comprising 2 to 10 carbons, and
$X^-$ is a negatively charged counterion.

14. The amine polymer of claim 13, wherein the amine polymer consists essentially of a homopolymer chain of the first repeat unit linked to a monomeric alkoxy end group or a monomeric aryloxy end group.

15. The amine polymer of claim 14, wherein the amine polymer has a degree of polymerization of about 15 to about 45.

16. The amine polymer of claim 14, wherein the amine polymer has a minimum inhibitory concentration (MIC) in water against *Escherichia coli* of about 30 mg/L to about 125 mg/L.

17. The amine polymer of claim 14, wherein the amine polymer has a minimum inhibitory concentration (MIC) in water against *Staphylococcus aureus* of about 30 mg/L to about 125 mg/L.

18. The amine polymer of claim 14, wherein the first repeat unit has a structure

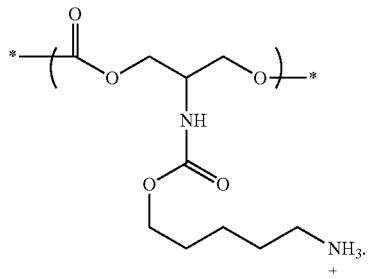

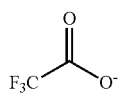

19. The amine polymer of claim 14, wherein the amine polymer has a structure

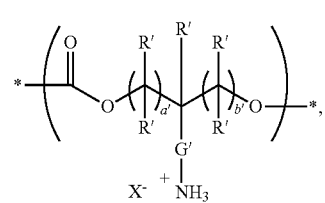

wherein x' is a positive integer having a value of about 15 to about 30.

20. The amine polymer of claim 13, wherein the amine polymer is a linear random copolymer consisting essentially of i) the first repeat unit, ii) a hydrophobic second repeat unit comprising an ester or carbonate backbone group, and iii) a monomeric alkoxy end group or monomeric aryloxy end group.

21. The amine polymer of claim 20, wherein the linear random copolymer has a degree of polymerization of about 10 to about 30.

22. A method, comprising:
providing a mixture comprising i) a first cyclic carbonate monomer, ii) a nucleophilic initiator for ring opening polymerization, iii) an organocatalyst, and iv) a solvent, wherein the first cyclic carbonate monomer has a structure according to formula (6):

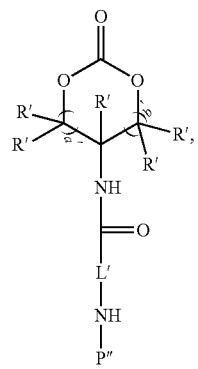

wherein a' is an integer equal to 1 or 2, b' is an integer equal to 1 or 2, each R' is an independent monovalent radical selected from the group consisting of hydrogen, methyl, and ethyl, L' is a divalent linking group comprising 2 to 10 carbons, and P'" is a primary amine protecting group;

agitating the mixture, thereby forming a protected amine polymer by a ring opening polymerization; and deprotecting the protected amine polymer, thereby forming an antimicrobial amine polymer.

23. A method, comprising:
forming an aqueous mixture containing an amine polymer comprising a first repeat unit of formula (2):

$$\left( \begin{array}{c} O \\ \parallel \\ * - C - O + \begin{array}{c} R' \\ | \\ C \\ | \\ R' \end{array} \Big)_{a'} \begin{array}{c} R' \\ | \\ C \\ | \\ R' \end{array} \Big)_{b'} O \end{array} \right)_{*}$$

$$X^- \quad {}^+NH_3$$

(2)

wherein a' is an integer equal to 1 or 2, b' is an integer equal to 1 or 2, each R' is an independent monovalent radical selected from the group consisting of hydrogen, methyl, and ethyl, G' is a divalent linking group comprising i) at least one carbon and ii) a nitrogen bonded to the backbone of the amine polymer, and X⁻ is a negatively charged counterion;

forming a second aqueous mixture comprising an anionic drug; and combining the first mixture and the second mixture, thereby forming an antimicrobial composition, wherein the amine polymer and the drug are bound by non-covalent interactions.

24. A method of treating a microbe, comprising contacting the microbe with the composition of claim 1, thereby killing the microbe.

25. A method, comprising:
disposing the composition of claim 1 on a surface of a substrate and removing any solvent, thereby forming an antimicrobial layer on the surface of the substrate.

26. The method of claim 25, wherein the substrate is a medical device.

27. An article comprising the composition of claim 1 disposed on a surface of a medical device.

28. The article of claim 27, wherein the medical device is a catheter.

29. The article of claim 27, wherein the medical device is a material suitable for a wound dressing.

30. An antimicrobial amine polymer, comprising a first repeat unit having a structure

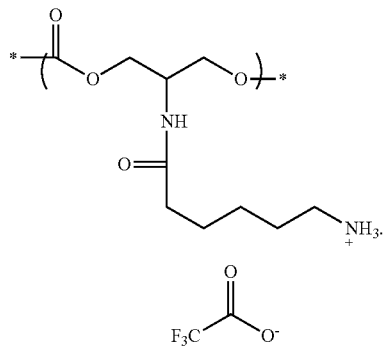

31. The amine polymer of claim 30, wherein the amine polymer has a structure

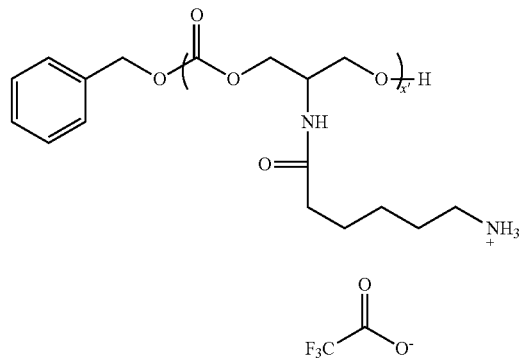

wherein x' is a positive integer having a value of about 15 to about 30.

* * * * *